(12) United States Patent
Pradhan et al.

(10) Patent No.: US 11,492,667 B2
(45) Date of Patent: Nov. 8, 2022

(54) COMPOSITIONS AND METHODS FOR DETECTING MOLECULAR TARGETS ON CHROMOSOMAL DNA

(71) Applicant: New England Biolabs, Inc., Ipswich, MA (US)

(72) Inventors: Sriharsa Pradhan, Ipswich, MA (US); Hang Gyeong Chin, Ipswich, MA (US); George R. Feehery, West Newbury, MA (US); Shuang-Yong Xu, Lexington, MA (US); Vishnu Udayakumaran Nair Sunitha Kumary, Ipswich, MA (US); Julie Beaulieu, Essex, MA (US); Pierre O. Esteve, Ipswich, MA (US)

(73) Assignee: New England Biolabs, Inc., Ipswich, MA (US)

( * ) Notice: Subject to any disclaimer, the term of this patent is extended or adjusted under 35 U.S.C. 154(b) by 0 days.

(21) Appl. No.: 17/342,216

(22) Filed: Jun. 8, 2021

(65) Prior Publication Data
US 2021/0388434 A1 Dec. 16, 2021

Related U.S. Application Data

(60) Provisional application No. 63/038,469, filed on Jun. 12, 2020.

(51) Int. Cl.
C12Q 1/6869 (2018.01)
C07K 14/31 (2006.01)
C12N 9/22 (2006.01)

(52) U.S. Cl.
CPC ............ C12Q 1/6869 (2013.01); C07K 14/31 (2013.01); C12N 9/22 (2013.01); C07K 2319/00 (2013.01)

(58) Field of Classification Search
None
See application file for complete search history.

(56) References Cited

U.S. PATENT DOCUMENTS

| 5,264,343 | A | 11/1993 | Krystosek et al. |
| 6,191,267 | B1 | 2/2001 | Kong et al. |
| 7,011,966 | B2 | 3/2006 | Samuelson et al. |
| 7,081,358 | B2 | 7/2006 | Heiter et al. |
| 7,790,379 | B2 | 9/2010 | Laemmli et al. |
| 7,820,424 | B2 | 10/2010 | Xu et al. |
| 7,943,303 | B2 | 5/2011 | Xu et al. |
| 8,163,529 | B2 | 4/2012 | Xu et al. |
| 2005/0136462 | A1 | 6/2005 | Zhu et al. |
| 2008/0268507 | A1 | 10/2008 | Xu et al. |
| 2017/0218349 | A1 | 8/2017 | Miller et al. |
| 2018/0250424 | A1 | 9/2018 | Cotta-Ramusino |
| 2019/0153435 | A1 | 5/2019 | Guan et al. |
| 2019/0211404 | A1 | 7/2019 | Ponnaluri et al. |

FOREIGN PATENT DOCUMENTS

| WO | 2006047183 A3 | 8/2006 |
| WO | 2018045141 A1 | 3/2018 |

OTHER PUBLICATIONS

Nilson et al.."Protein L from Peptostreptococcus magnus Binds to the kappa light chain variable domain", The Journal of Biological Chemistry, vol. 267, No. 4, pp. 2234-2239 (Year: 1992).*
Van Steensal, et al. Nat. Biotechnology, 2000, 18: 424-8.
Montalbano et al. Mol. Cell. 2017; 68(1): 44-59.
Thiry, DNA Cell Biol. 1991, 169-80.
Thiry, Histochem CytoChem 1991, 871-4.
Schmid et al. Mol Cell. 2004;16(1):147-57.
Chan et al., Nucleic Acids Research, 2004 32: 6187-6199.
Sasnauskas, et al, Nucleic Acid Research (2017) 45, 9583-9594.
Rigby, et al. 1977, Journal of Molecular Biology vol. 113, 237-251.
Esteve et al. (2006) Genes & Development 20: 3089-3103.
Ponnaluri, et al., Genome Biology, 18, 122, 2017.
Gutjahr, et al., Nucleic Acids Research, 42, 9, e77, 2014.
Bellamy, et al. J. Mol. Biol. 2005 345, 641-653.
Chan, Nucl. Acids Res. 2004 32, 6187-6199.
Chmuzh, et al., Biotekhnologiya 3: 22-26, 2005.

(Continued)

Primary Examiner — Anand U Desai
(74) Attorney, Agent, or Firm — New England Biolabs, Inc; Harriet M. Strimpel

(57) ABSTRACT

Compositions, methods and kits are provided for identifying the presence and location of a target in chromosomal DNA. A nicking endonuclease fused to a binding domain that binds to a constant region of an antibody (NEFP) is provided that may be used for binding to a target directly or via an antibody that binds to the target. The target may be a protein or structural feature of the DNA and its presence and location may correspond to a phenotype and/or pathology in a biopsy or other cell sample for diagnostic purposes. The background is reduced by the addition of a glycoaminoglycan (GAG) that reversibly inhibits binding of the NEFP to DNA. Nick translation in the presence of a strand displacing polymerase enables the incorporation of tagged nucleotides that (i) blocks re-nicking; (ii) facilitates immobilization of DNA fragments around the target for sequencing; and/or (iii) enables dye labelling of the chromosomal DNA within the cell nuclei for analysis by microscopy.

14 Claims, 18 Drawing Sheets
(9 of 18 Drawing Sheet(s) Filed in Color)
Specification includes a Sequence Listing.

(56) References Cited

OTHER PUBLICATIONS

Cohen Karni, et al., Proc. Natl. Acad. Sci. U. S. A. 108:11040-11045 (2011).
Heiter, et al., J. Mol. Biol. 2005 348, 631-640.
Hsu, et al., Nature Biotechnology 2013 31: 827-832.
Jo, et al., PNAS 2007 104:2673-2678.
Morgan, et al., Biol. Chem. 2000 381, 1123-1125.
Samuelson, et al., Nucl. Acids Res. 2004 32, 3661-3671.
Sasnauskas, Proc. Natl. Acad. Sci. USA 2003 100, 6410-6415.
Xiao, et al., Nucleic Acids Res. 2007 35:e16.
Xu et al., Sci. Rep. 6:28579, 2016.
Xu, et al., Proc. Natl. Acad. Sci. USA 2001 98, 12990-12995.
Zheleznaya et al Biochemistry (Mosc). Dec. 2009;74(13):1457-66.
Zhu, et al., J. Mol. Biol. 2004 337, 573-583.

\* cited by examiner

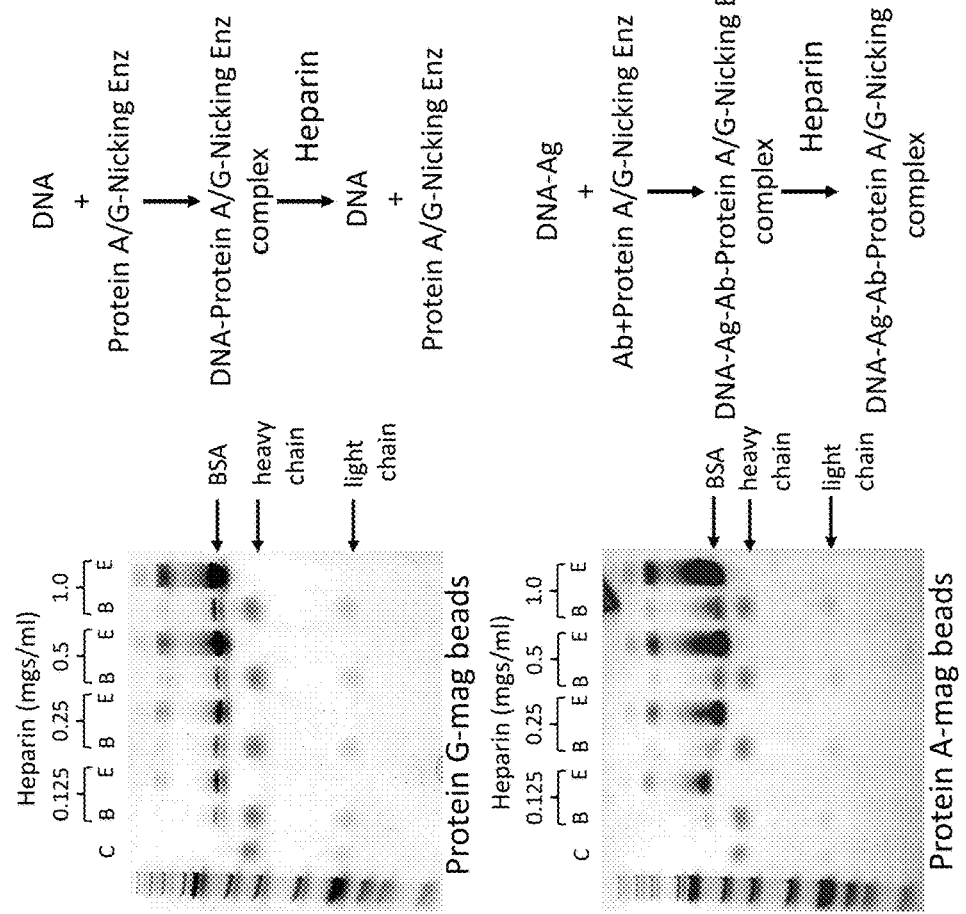

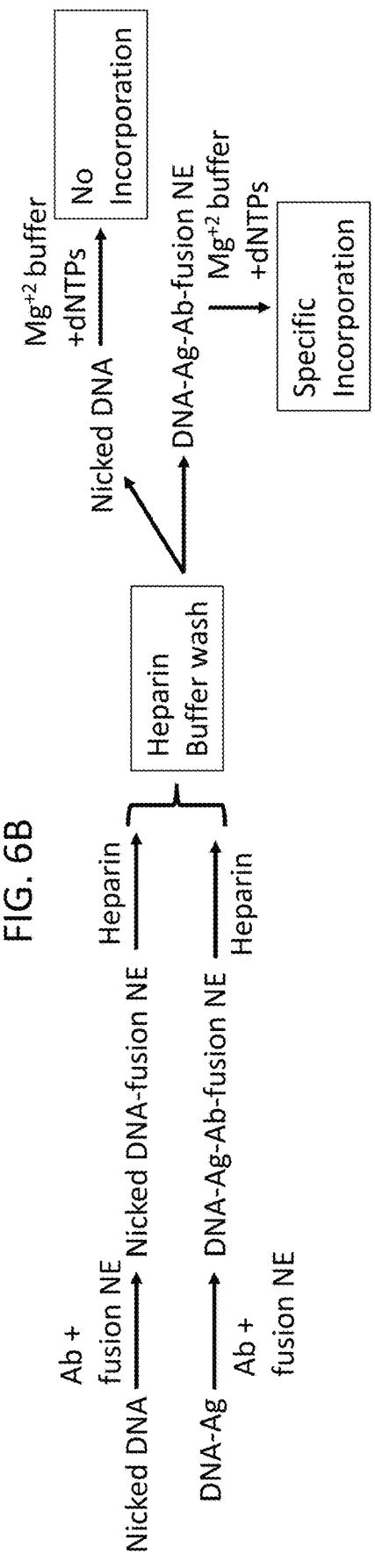
FIG. 6A
FIG. 6B

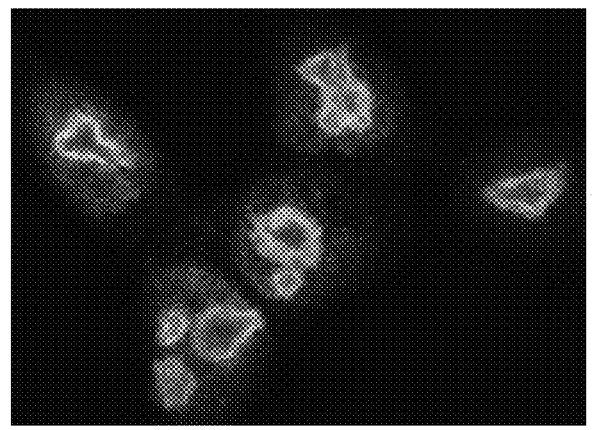
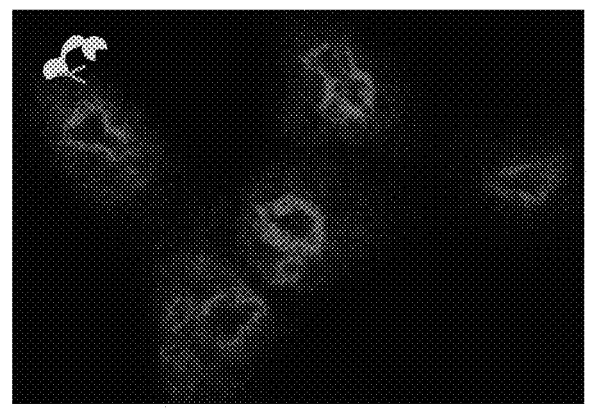
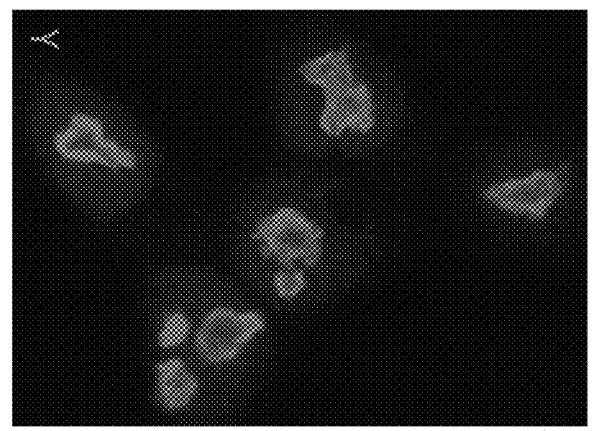
Anti-NPM1 (protein localization) Using only antibody immunocytochemistry
NEA-vi w DNA labeling) Using Texas Red dATP
NPM1-NEAT-S q merged)
FIG. 7B

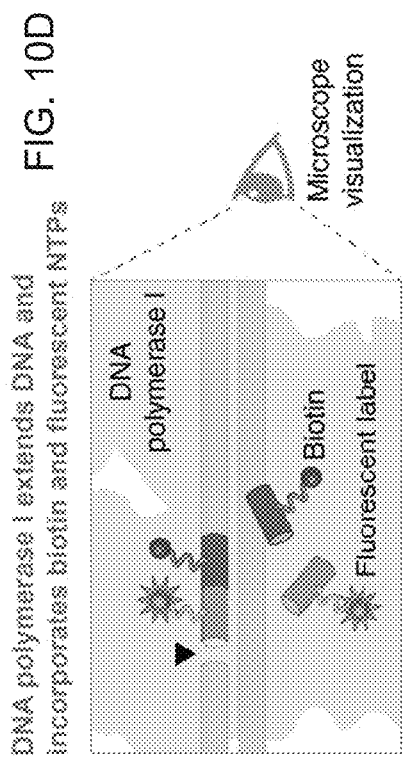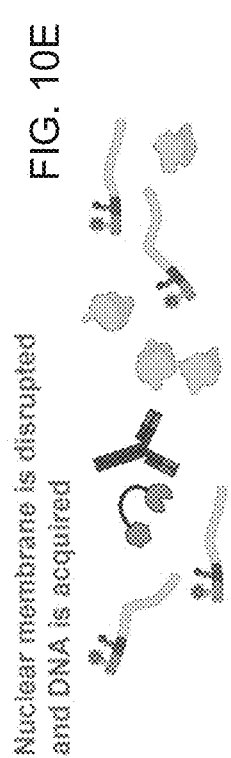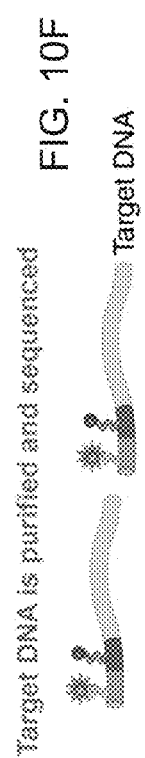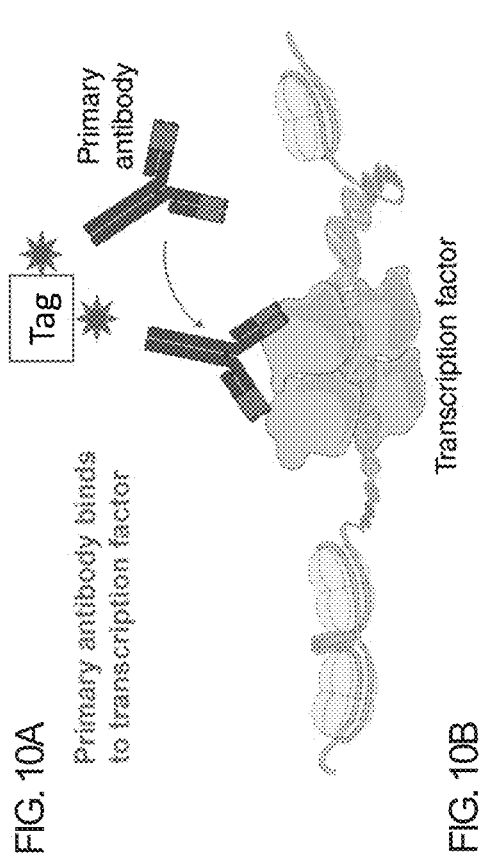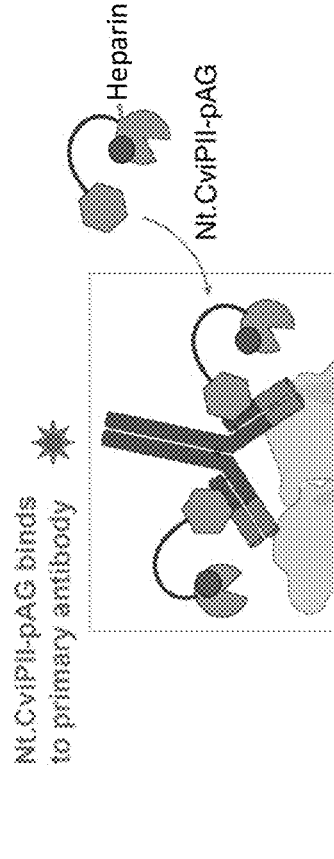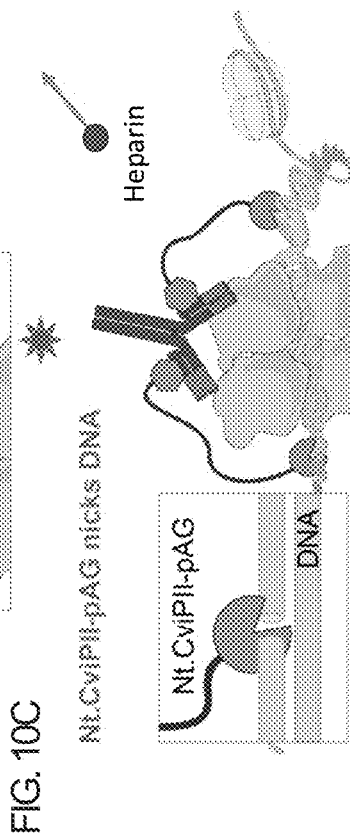

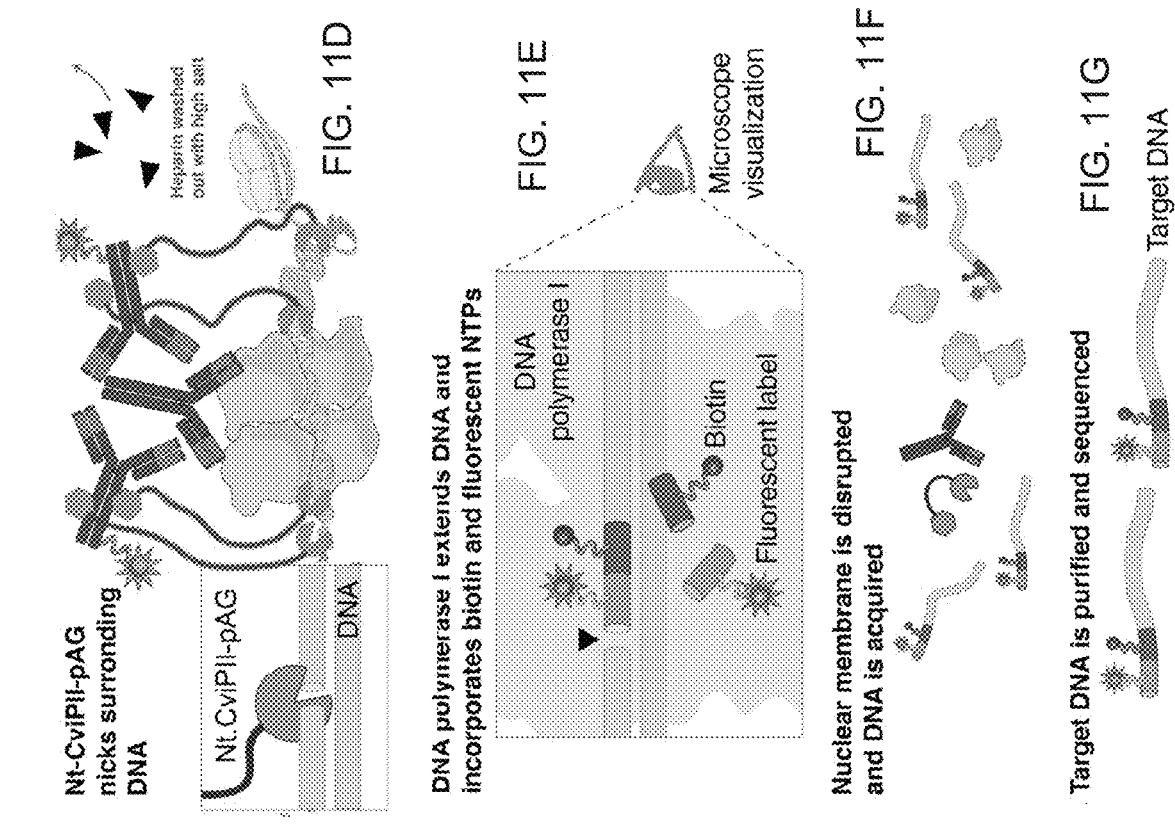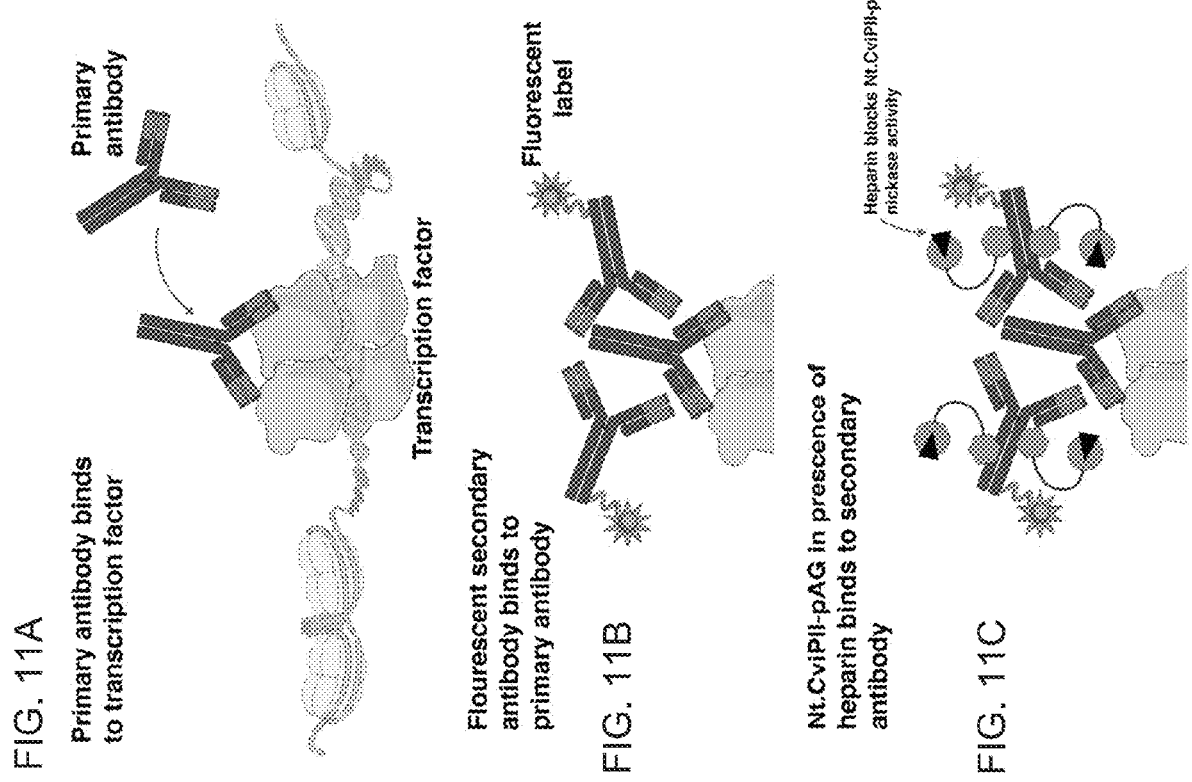

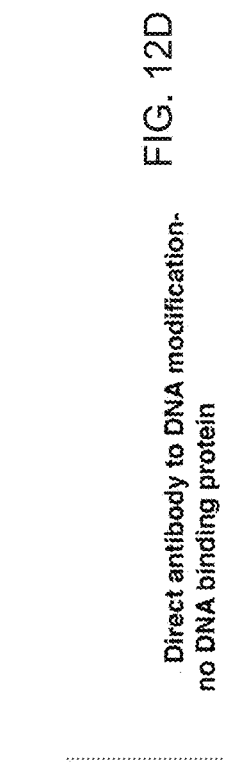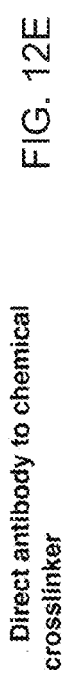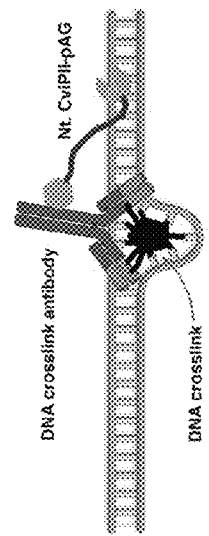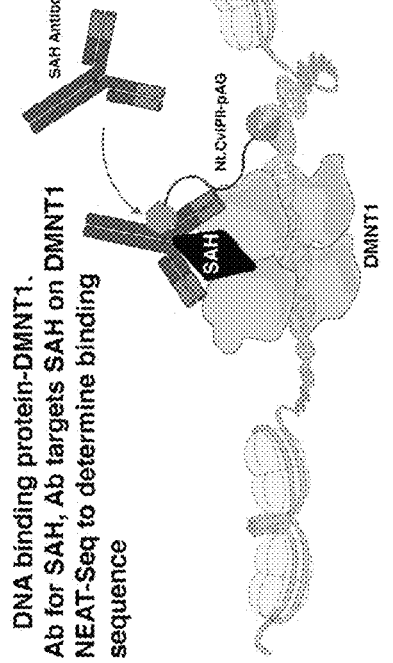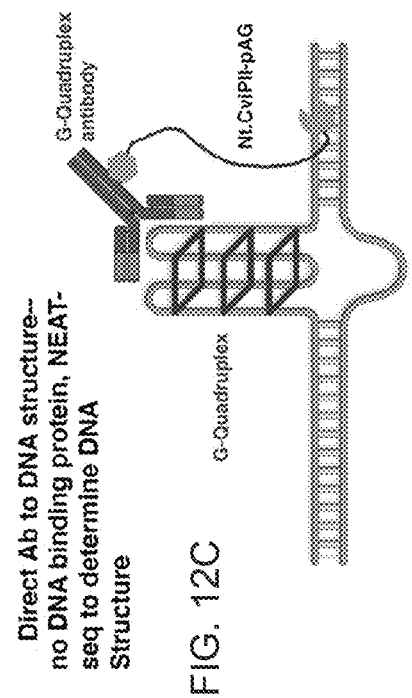

FIG. 12A
DNA binding protein-DMNT1. Ab for SAH, Ab targets SAH on DMNT1 NEAT-Seq to determine binding sequence FIG. 12B
No antibody to protein affinity peptide/protein fused to nicking enzyme—NEAT-seq to determine binding sequence FIG. 12C
Direct Ab to DNA structure—no DNA binding protein, NEAT-seq to determine DNA Structure FIG. 12D
Direct antibody to DNA modification- no DNA binding protein FIG. 12E
Direct antibody to chemical crosslinker Lamin-NEAT-seq merged)

NEAT-view DNA labeling using Texas Red dATP

Anti-Lamin (protein localization)

FIG. 15E
Peak nos.
NEAT-Seq: 7655
Dam-ID: 7632
Protect-seq: 7441
ChIP-seq: 3154
FIG. 15F
Common peaks (%)
NEAT-Seq vs. Dam-ID: 91.7%
NEAT-Seq vs. Protect-seq: 91.5%
NEAT-Seq vs. ChIP-seq: 38.4%
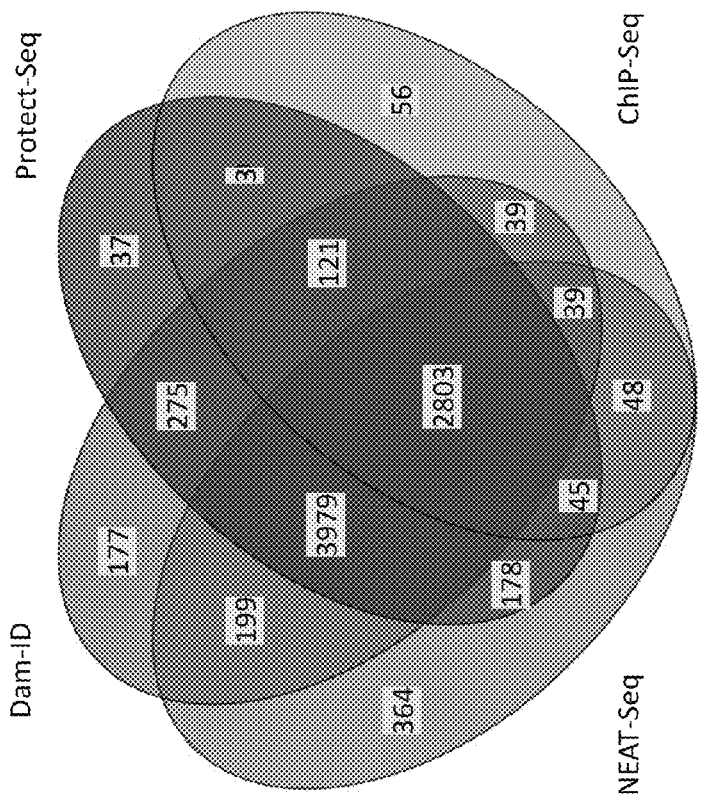
FIG. 15D
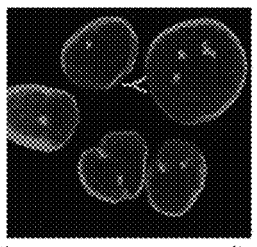
FIG. 15A
Anti-Lamin B2 (protein localization)
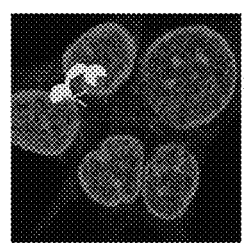
FIG. 15B
NEAT-View (DNA labeling) using Texas Red dATP
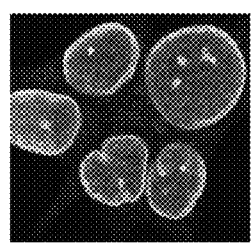
FIG. 15C
Lamin B2-NEAT-View (merged)

SEQUENCE LISTING

```
<160> NUMBER OF SEQ ID NOS: 9

<210> SEQ ID NO 1
<211> LENGTH: 6
<212> TYPE: PRT
<213> ORGANISM: Artificial Sequence
<220> FEATURE:
<223> OTHER INFORMATION: Synthetic construct

<400> SEQUENCE: 1

Gly Ser Ala Thr Ile Val
1               5

<210> SEQ ID NO 2
<211> LENGTH: 12
<212> TYPE: PRT
<213> ORGANISM: Artificial Sequence
<220> FEATURE:
<223> OTHER INFORMATION: Synthetic construct

<400> SEQUENCE: 2

Gly Ser Ala Thr Gly Thr Ser Ala Gly Ser Thr Gly
1               5                   10

<210> SEQ ID NO 3
<211> LENGTH: 6
<212> TYPE: PRT
<213> ORGANISM: Artificial Sequence
<220> FEATURE:
<223> OTHER INFORMATION: Synthetic construct

<400> SEQUENCE: 3

Gly Ser Gly Ser Gly Ser
1               5

<210> SEQ ID NO 4
<211> LENGTH: 126
<212> TYPE: PRT
<213> ORGANISM: Artificial Sequence
<220> FEATURE:
<223> OTHER INFORMATION: Synthetic construct

<400> SEQUENCE: 4

Lys Lys Pro Leu Arg Pro Cys Cys Glu Phe His Cys Tyr Asn Leu Thr
1               5                   10                  15

Arg Glu Arg Tyr Cys Glu Glu His Arg Tyr Lys Glu Lys Glu Thr Gln
            20                  25                  30

Gln Asp Lys Asn Arg Tyr Tyr Asp Arg Phe Lys Arg Asp Lys Glu Ser
        35                  40                  45

Thr Ala Phe Tyr Arg Ser Lys Ala Trp Glu Arg Leu Arg Glu Gln Ala
    50                  55                  60
```

Leu Met Arg Asp Lys Gly Leu Cys Leu His Cys Lys Asn Asn Arg Lys
65                  70                  75                  80

Ile Lys Val Ala Asp Met Val Asp His Ile Ile Pro Ile Lys Val Asp
                85                  90                  95

Pro Ser Leu Lys Leu Lys Leu Glu Asn Leu Gln Ser Leu Cys Asn Pro
            100                 105                 110

Cys His Asn Arg Lys Thr Ala Glu Asp Lys Lys Lys Tyr Gly
        115                 120                 125

<210> SEQ ID NO 5
<211> LENGTH: 317
<212> TYPE: PRT
<213> ORGANISM: Artificial Sequence
<220> FEATURE:
<223> OTHER INFORMATION: Synthetic construct

<400> SEQUENCE: 5

Met Lys Gly Glu Thr Thr Thr Glu Ala Val Asp Ala Ala Thr Ala Glu
1               5                   10                  15

Lys Val Phe Lys Gln Tyr Ala Asn Asp Asn Gly Val Asp Gly Glu Trp
            20                  25                  30

Thr Tyr Asp Asp Ala Thr Lys Thr Phe Thr Val Thr Glu Lys Pro Glu
        35                  40                  45

Val Ile Asp Ala Ser Glu Leu Thr Pro Ala Val Thr Thr Tyr Lys Leu
50                  55                  60

Val Ile Asn Gly Lys Thr Leu Lys Gly Glu Thr Thr Thr Glu Ala Val
65                  70                  75                  80

Asp Ala Ala Thr Ala Glu Lys Val Phe Lys Gln Tyr Ala Asn Asp Asn
                85                  90                  95

Gly Val Asp Gly Glu Trp Thr Tyr Asp Asp Ala Thr Lys Thr Phe Thr
            100                 105                 110

Val Thr Glu Lys Pro Glu Val Ile Asp Ala Ser Glu Leu Thr Pro Ala
        115                 120                 125

Val Thr Thr Tyr Lys Leu Val Ile Asn Gly Lys Thr Leu Lys Gly Glu
        130                 135                 140

Thr Thr Thr Lys Ala Val Asp Ala Glu Thr Ala Glu Lys Ala Phe Lys
145                 150                 155                 160

Gln Tyr Ala Asn Asp Asn Gly Val Asp Gly Val Trp Thr Tyr Asp Asp
            165                 170                 175

Ala Thr Lys Thr Phe Thr Val Thr Glu Gly Ser Ala Thr Ile Val Lys
            180                 185                 190

Lys Pro Leu Arg Pro Cys Cys Glu Phe His Cys Tyr Asn Leu Thr Arg
            195                 200                 205

Glu Arg Tyr Cys Glu Glu His Arg Tyr Lys Glu Lys Glu Thr Gln Gln
            210                 215                 220

Asp Lys Asn Arg Tyr Tyr Asp Arg Phe Lys Arg Asp Lys Glu Ser Thr
225                 230                 235                 240

Ala Phe Tyr Arg Ser Lys Ala Trp Glu Arg Leu Arg Glu Gln Ala Leu
            245                 250                 255

Met Arg Asp Lys Gly Leu Cys Leu His Cys Lys Asn Asn Arg Lys Ile
            260                 265                 270

Lys Val Ala Asp Met Val Asp His Ile Ile Pro Ile Lys Val Asp Pro
        275                 280                 285

Ser Leu Lys Leu Lys Leu Glu Asn Leu Gln Ser Leu Cys Asn Pro Cys
        290                 295                 300

His Asn Arg Lys Thr Ala Glu Asp Lys Lys Tyr Gly
305                 310                 315

<210> SEQ ID NO 6
<211> LENGTH: 373
<212> TYPE: PRT
<213> ORGANISM: Artificial Sequence
<220> FEATURE:
<223> OTHER INFORMATION: Synthetic construct

<400> SEQUENCE: 6

Ala Ala Gln His Asp Glu Ala Gln Gln Asn Ala Phe Tyr Gln Val Leu
1               5                   10                  15

Asn Met Pro Asn Leu Asn Ala Asp Gln Arg Asn Gly Phe Ile Gln Ser
            20                  25                  30

Leu Lys Asp Asp Pro Ser Gln Ser Ala Asn Val Leu Gly Glu Ala Gln
        35                  40                  45

Lys Leu Asn Asp Ser Gln Ala Pro Lys Ala Asp Ala Gln Gln Asn Lys
    50                  55                  60

Phe Asn Lys Asp Gln Gln Ser Ala Phe Tyr Glu Ile Leu Asn Met Pro
65                  70                  75                  80

Asn Leu Asn Glu Glu Gln Arg Asn Gly Phe Ile Gln Ser Leu Lys Asp
                85                  90                  95

Asp Pro Ser Gln Ser Thr Asn Val Leu Gly Glu Ala Lys Lys Leu Asn
            100                 105                 110

Glu Ser Gln Ala Pro Lys Ala Asp Asn Asn Phe Asn Lys Glu Gln Gln
        115                 120                 125

Asn Ala Phe Tyr Glu Ile Leu Asn Met Pro Asn Leu Asn Glu Glu Gln
130                 135                 140

Arg Asn Gly Phe Ile Gln Ser Leu Lys Asp Asp Pro Ser Gln Ser Ala
145                 150                 155                 160

Asn Leu Leu Ala Glu Ala Lys Lys Leu Asn Asp Ala Gln Ala Pro Lys
                165                 170                 175

Ala Asp Asn Lys Phe Asn Lys Glu Gln Gln Asn Ala Phe Tyr Glu Ile
            180                 185                 190

Leu His Leu Pro Asn Leu Thr Glu Glu Gln Arg Asn Gly Phe Ile Gln
        195                 200                 205

Ser Leu Lys Asp Asp Pro Ser Val Ser Lys Glu Ile Leu Ala Glu Ala
    210                 215                 220

Lys Lys Leu Asn Asp Ala Gln Ala Pro Lys Glu Gly Ser Ala Thr Gly
225                 230                 235                 240

Thr Ser Ala Gly Ser Thr Gly Lys Lys Pro Leu Arg Pro Cys Cys Glu
                245                 250                 255

Phe His Cys Tyr Asn Leu Thr Arg Glu Arg Tyr Cys Glu Glu His Arg
            260                 265                 270

Tyr Lys Glu Lys Glu Thr Gln Gln Asp Lys Asn Arg Tyr Tyr Asp Arg
        275                 280                 285

Phe Lys Arg Asp Lys Glu Ser Thr Ala Phe Tyr Arg Ser Lys Ala Trp
    290                 295                 300

Glu Arg Leu Arg Glu Gln Ala Leu Met Arg Asp Lys Gly Leu Cys Leu
305                 310                 315                 320

His Cys Lys Asn Asn Arg Lys Ile Lys Val Ala Asp Met Val Asp His
                325                 330                 335

Ile Ile Pro Ile Lys Val Asp Pro Ser Leu Lys Leu Lys Leu Glu Asn
            340                 345                 350

```
Leu Gln Ser Leu Cys Asn Pro Cys His Asn Arg Lys Thr Ala Glu Asp
        355                 360                 365

Lys Lys Lys Tyr Gly
        370

<210> SEQ ID NO 7
<211> LENGTH: 539
<212> TYPE: PRT
<213> ORGANISM: Artificial Sequence
<220> FEATURE:
<223> OTHER INFORMATION: Synthetic construct

<400> SEQUENCE: 7

Met Lys Gly Glu Thr Thr Thr Glu Ala Val Asp Ala Ala Thr Ala Glu
1               5                   10                  15

Lys Val Phe Lys Gln Tyr Ala Asn Asp Asn Gly Val Asp Gly Glu Trp
            20                  25                  30

Thr Tyr Asp Asp Ala Thr Lys Thr Phe Thr Val Thr Glu Lys Pro Glu
        35                  40                  45

Val Ile Asp Ala Ser Glu Leu Thr Pro Ala Val Thr Thr Tyr Lys Leu
    50                  55                  60

Val Ile Asn Gly Lys Thr Leu Lys Gly Glu Thr Thr Thr Glu Ala Val
65                  70                  75                  80

Asp Ala Ala Thr Ala Glu Lys Val Phe Lys Gln Tyr Ala Asn Asp Asn
                85                  90                  95

Gly Val Asp Gly Glu Trp Thr Tyr Asp Asp Ala Thr Lys Thr Phe Thr
            100                 105                 110

Val Thr Glu Lys Pro Glu Val Ile Asp Ala Ser Glu Leu Thr Pro Ala
        115                 120                 125

Val Thr Thr Tyr Lys Leu Val Ile Asn Gly Lys Thr Leu Lys Gly Glu
    130                 135                 140

Thr Thr Thr Lys Ala Val Asp Ala Glu Thr Ala Glu Lys Ala Phe Lys
145                 150                 155                 160

Gln Tyr Ala Asn Asp Asn Gly Val Asp Gly Val Trp Thr Tyr Asp Asp
                165                 170                 175

Ala Thr Lys Thr Phe Thr Val Thr Glu Gly Ser Ala Thr Ile Val Met
            180                 185                 190

Tyr Ile Tyr Met Ser Thr Pro Gln Ala Lys Thr Lys Tyr Tyr Glu Gln
        195                 200                 205

Arg Phe Val Asn Asp Phe Tyr Lys Glu Leu Glu Arg Asn Lys Val Ser
    210                 215                 220

Leu Pro Val Thr Ile Val Leu Lys Asp Asn Leu Gly Ile Lys Gln Val
225                 230                 235                 240

Ile Gln Asn Gly Ser Gly Val Arg Val Leu Arg Asp Lys Ala Asn Ala
                245                 250                 255

Lys Ser Pro Ser Lys Ile Lys Ser Glu Glu Leu Gly Arg His Val Thr
            260                 265                 270

Ser Lys Ala Asp Ile Ala Leu Phe Thr Glu Glu Lys Asn Gly Thr Lys
        275                 280                 285

Val Asp Val Ala Trp Ile Ser Pro Gln Ser His Lys Asp Phe Leu Gly
    290                 295                 300

Lys Lys Ile Thr Pro Ala Gln Tyr Phe Asp Ala Ser Ser Asp Val Met
305                 310                 315                 320

Phe Lys Thr Lys Ile Gly Gln Pro Lys Glu Ile Lys Glu Leu Lys Asn
                325                 330                 335
```

```
Lys Met Ile Ser Leu Ser Val Pro Leu Thr Ala Thr Lys Tyr Cys Trp
                340                 345                 350

Pro Lys Tyr Lys Ser Gly Thr Ser Leu Arg Ile Trp Asp Val Gln
            355                 360                 365

Ser Thr Ile Leu Met Asn Met Ala Ile Phe Gly Val Glu Phe Gly Lys
        370                 375                 380

Ala Tyr Cys Arg Asn Asn Ala Asn Ile Leu Met Val Gly Asp Pro Leu
385                 390                 395                 400

Ile Glu Val Lys Asp Asp Lys Thr Ile Ile Leu Thr Thr Lys Glu Asn
                405                 410                 415

Gly Phe Ser Leu Ala Asn Gly Phe Ala Glu Tyr Ile Pro Ser Lys Asp
            420                 425                 430

Lys Pro Ile Phe Phe Thr Lys Pro Thr Ser Gly Lys Lys Thr Val Val
        435                 440                 445

Asp Gly Lys Thr Ile Glu Gly Val Ser Val Trp Ile Ile Tyr Arg Ser
    450                 455                 460

Tyr Ala Gly Ser Lys Asn Arg Lys Ile Asp Asp Val Leu Lys Asn Lys
465                 470                 475                 480

Ile Glu Leu Ile Ser Ser Cys Ser Val Lys Lys Asp Asn Phe
                485                 490                 495

Val Ser Ile Met Gln Ser Lys Lys Ile Thr Ser Pro Pro Lys Ser Lys
        500                 505                 510

Lys Ile Thr Ser Pro Pro Lys Ser Lys Ile Thr Ser Pro Ser Lys
            515                 520                 525

Ser Lys Lys Ile Thr Asn Phe Phe Met Lys Lys
        530                 535

<210> SEQ ID NO 8
<211> LENGTH: 595
<212> TYPE: PRT
<213> ORGANISM: Artificial Sequence
<220> FEATURE:
<223> OTHER INFORMATION: Synthetic construct

<400> SEQUENCE: 8

Ala Ala Gln His Asp Glu Ala Gln Gln Asn Ala Phe Tyr Gln Val Leu
1               5                   10                  15

Asn Met Pro Asn Leu Asn Ala Asp Gln Arg Asn Gly Phe Ile Gln Ser
            20                  25                  30

Leu Lys Asp Asp Pro Ser Gln Ser Ala Asn Val Leu Gly Glu Ala Gln
        35                  40                  45

Lys Leu Asn Asp Ser Gln Ala Pro Lys Ala Asp Ala Gln Gln Asn Lys
    50                  55                  60

Phe Asn Lys Asp Gln Gln Ser Ala Phe Tyr Glu Ile Leu Asn Met Pro
65                  70                  75                  80

Asn Leu Asn Glu Glu Gln Arg Asn Gly Phe Ile Gln Ser Leu Lys Asp
                85                  90                  95

Asp Pro Ser Gln Ser Thr Asn Val Leu Gly Glu Ala Lys Lys Leu Asn
            100                 105                 110

Glu Ser Gln Ala Pro Lys Ala Asp Asn Phe Asn Lys Glu Gln Gln
        115                 120                 125

Asn Ala Phe Tyr Glu Ile Leu Asn Met Pro Asn Leu Asn Glu Glu Gln
    130                 135                 140

Arg Asn Gly Phe Ile Gln Ser Leu Lys Asp Asp Pro Ser Gln Ser Ala
145                 150                 155                 160
```

```
Asn Leu Leu Ala Glu Ala Lys Leu Asn Asp Ala Gln Ala Pro Lys
                165                 170                 175

Ala Asp Asn Lys Phe Asn Lys Glu Gln Gln Asn Ala Phe Tyr Glu Ile
            180                 185                 190

Leu His Leu Pro Asn Leu Thr Glu Glu Gln Arg Asn Gly Phe Ile Gln
                195                 200                 205

Ser Leu Lys Asp Asp Pro Ser Val Ser Lys Glu Ile Leu Ala Glu Ala
    210                 215                 220

Lys Lys Leu Asn Asp Ala Gln Ala Pro Lys Glu Gly Ser Ala Thr Gly
225                 230                 235                 240

Thr Ser Ala Gly Ser Thr Gly Met Tyr Ile Tyr Met Ser Thr Pro Gln
                245                 250                 255

Ala Lys Thr Lys Tyr Tyr Glu Gln Arg Phe Val Asn Asp Phe Tyr Lys
            260                 265                 270

Glu Leu Glu Arg Asn Lys Val Ser Leu Pro Val Thr Ile Val Leu Lys
        275                 280                 285

Asp Asn Leu Gly Ile Lys Gln Val Ile Gln Asn Gly Ser Gly Val Arg
    290                 295                 300

Val Leu Arg Asp Lys Ala Asn Ala Lys Ser Pro Ser Lys Ile Lys Ser
305                 310                 315                 320

Glu Glu Leu Gly Arg His Val Thr Ser Lys Ala Asp Ile Ala Leu Phe
                325                 330                 335

Thr Glu Glu Lys Asn Gly Thr Lys Val Asp Val Ala Trp Ile Ser Pro
            340                 345                 350

Gln Ser His Lys Asp Phe Leu Gly Lys Lys Ile Thr Pro Ala Gln Tyr
        355                 360                 365

Phe Asp Ala Ser Ser Asp Val Met Phe Lys Thr Lys Ile Gly Gln Pro
    370                 375                 380

Lys Glu Ile Lys Glu Leu Lys Asn Lys Met Ile Ser Leu Ser Val Pro
385                 390                 395                 400

Leu Thr Ala Thr Lys Tyr Cys Trp Pro Lys Tyr Lys Ser Gly Thr Ser
                405                 410                 415

Leu Arg Ile Trp Asp Asp Val Gln Ser Thr Ile Leu Met Asn Met Ala
            420                 425                 430

Ile Phe Gly Val Glu Phe Gly Lys Ala Tyr Cys Arg Asn Asn Ala Asn
        435                 440                 445

Ile Leu Met Val Gly Asp Pro Leu Ile Glu Val Lys Asp Asp Lys Thr
    450                 455                 460

Ile Ile Leu Thr Thr Lys Glu Asn Gly Phe Ser Leu Ala Asn Gly Phe
465                 470                 475                 480

Ala Glu Tyr Ile Pro Ser Lys Asp Lys Pro Ile Phe Phe Thr Lys Pro
                485                 490                 495

Thr Ser Gly Lys Lys Thr Val Val Asp Gly Lys Thr Ile Glu Gly Val
            500                 505                 510

Ser Val Trp Ile Ile Tyr Arg Ser Tyr Ala Gly Ser Lys Asn Arg Lys
        515                 520                 525

Ile Asp Asp Val Leu Lys Asn Lys Ile Glu Leu Ile Ser Ser Ser Cys
    530                 535                 540

Ser Val Lys Lys Lys Asp Asn Phe Val Ser Ile Met Gln Ser Lys Lys
545                 550                 555                 560

Ile Thr Ser Pro Pro Lys Ser Lys Lys Ile Thr Ser Pro Pro Lys Ser
                565                 570                 575
```

```
Lys Lys Ile Thr Ser Pro Ser Lys Ser Lys Ile Thr Asn Phe Phe
            580                 585                 590
Met Lys Lys
        595

<210> SEQ ID NO 9
<211> LENGTH: 30
<212> TYPE: DNA
<213> ORGANISM: Artificial Sequence
<220> FEATURE:
<223> OTHER INFORMATION: Synthetic construct

<400> SEQUENCE: 9
ccagatcgtt caccagtaca cagtaattcg                               30
```

COMPOSITIONS AND METHODS FOR DETECTING MOLECULAR TARGETS ON CHROMOSOMAL DNA

CROSS-REFERENCE

This application claims priority from U.S. Provisional Application No. 63/038,469, filed Jun. 12, 2020, herein incorporated by reference.

SEQUENCE LISTING STATEMENT

This application includes a Sequence Listing submitted electronically in ascii format under the file name "NEB-428_ST25.txt". This Sequence Listing is incorporated herein in its entirety by this reference.

BACKGROUND

When a patient is diagnosed with breast cancer, the diagnostic test may involve both molecular and morphological analysis of biopsied tissue samples. Generally, this analysis occurs in a histology lab on samples that have been fixed several days prior to the analysis. For example, the tissue may be stained using standard nucleus staining protocols to reveal changes in nuclear morphology. Antibodies may be employed to look for the presence of hormone receptors the absence of which suggests malignancy and also potential treatment protocols. Examples of targeted receptors include Her2, estrogen and progesterone receptors. If all are absent, the presumption is that a virulent cancer is present. Recently, a rapid diagnostic test has been developed that can be performed on living or fixed cells by an operating technician during surgery. This diagnostic test reveals globally, which regions of DNA in the nucleus are open chromatin. Changes in staining patterns in regions of open chromatin provide a rapid positive indicator for cancer (see for example, US 2019/0211404). This method does not however describe sequence specific data for specific DNA binding proteins (DBP) in the regions of open chromatin or for other target proteins associated with chromatin. Interactions between proteins and DNA in open chromatin have been analyzed using chromatin immunoprecipitation technique (ChIP) which is capable of localizing bound proteins to genomic loci with a resolution of about 0.5 kb. This method is performed on cells that have been fixed using formaldehyde. Other techniques include: Dam-ID (van Steensal et al. Nat. Biotechnology, 2000, 18: 424-8) and PinPoint (Montalbano et al. Mol. Cell. 2017; 68(1): 44-59). Nick translation has also been used to incorporate labeled nucleotides into interphase chromatin for imaging to differentiate active from inactive chromatin (see for example U.S. Pat. No. 5,264,343; Thiry, DNA Cell Biol. 1991, 169-80 and Thiry, Histochem CytoChem 1991, 871-4). These techniques that look at regions of active chromatin all suffer from at least one drawback that may include: a requirement for fixed cells, a relatively high cell number requirement for analysis, a high background signal, DNA damage; and/or insufficient resolution of target non-histone binding proteins on the DNA in active and inactive chromatin regions. An alternative approach to open chromatin scanning has been provided by U.S. Pat. No. 7,790,379, also Schmid, et al. Mol Cell. 2004; 16(1):147-57, that seeks to remedy the deficiencies described above. This method referred to as "cut and run" relies on antibodies tethered to DNases directly or indirectly that cleave double stranded DNA into small fragments in regions around DBP or chromatin. The "cut and run" method results in DNase cleaved DNA fragments that may include cleavage by untethered DNases. Careful titration of the DNase and incubation at low temperatures (4° C.) is required to prevent complete degradation of the DNA in open chromatin. The resulting DNA fragments diffuse out of the cells into extracellular fluid. The soluble extracellular DNA fragments can then be purified and sequenced. However, this method appears to require a large number of cells to overcome the diminished yield resulting from the reliance on diffused fragments. Such processes are inefficient and wasteful of materials.

SUMMARY

Methods and compositions are provided that relate to identifying a location of a target in/on chromosomal DNA obtained from a cell or contained within a cell in the form of chromatin.

In general, compositions are described that include a fusion protein characterized by a nicking endonuclease such as Nt.CviPII or gHNH and a domain that binds to a constant region of an antibody. Examples of a domain that binds to a constant region of an antibody include Protein A (pA), Protein L (pL) or Protein G (pG) or one or more of portions or the whole Protein A, G and/or L in tandem sequence. The fusion of a nicking endonuclease and a domain that binds the constant region of the antibody is here referred to as a nicking endonuclease fusion protein (NEFP). The term "NEFP" also refers to a nicking endonuclease and a domain that has affinity binding properties for binding directly to a target where the domain may be an agonist or antagonist of the target.

In one embodiment, the NEFP has at least 90% sequence identity to a sequence selected from the group consisting of: SEQ ID NOs: 5, 6, 7 and 8.

The composition may be provided as a lyophilized preparation, immobilized on beads or in solution in a buffer having a low concentration (for example, less than 100 mM salt) of an inorganic salt such as NaCl. The inorganic salt buffer described throughout should not contain magnesium or manganese ions unless specifically described for activating nicking. The composition may include in the buffer, an organic salt such as glycosaminoglycan (GAG) such as a heparin salt for acting as an inhibitory agent of the nicking endonuclease portion of the NEFP. The ratio of the heparin salt to NEFP is preferably greater than 1:1, for example, at least 10:1, for example at least 100:1. The composition may also include a polymerase such as a strand displacing polymerase either separately, in a mixture, or as part of the fusion protein to form a tripartite fusion protein.

In general, methods are described herein for identifying a target in or on chromosomal DNA that is diagnostic for a phenotype or pathological condition such as cancer.

In one embodiment, a method is provided for nicking chromosomal DNA, that includes the steps of: (a) combining the chromosomal DNA with a fusion protein comprising: a nicking endonuclease; and a binding domain that binds directly or indirectly to a target in the chromosomal DNA, to produce a reaction mix; and (b) incubating the reaction mix to nick the chromosomal DNA at sites that are proximal to the target.

In one example, the binding domain binds to the constant region of an antibody, and the fusion protein binds indirectly to the target via a target-specific antibody. In one example, binding of the nicking endonuclease to the chromosomal DNA by non-specific DNA binding or specific binding to recognition sequences in the DNA is prevented by for example, the use of a heparin salt in a low salt buffer.

The method may also include the step of combining the chromosomal DNA with a strand-displacing polymerase and dNTPs to nick translate the chromosomal DNA, wherein one or more dNTPs is modified for blocking secondary nicking and wherein optionally one or more nucleotides in the mixture is tagged for: (i) permitting visualization of the nicked translated DNA by microscopy; and/or (ii) immobilizing the nicked translated DNA on a matrix.

The method may further include identifying the location of the target on the DNA by sequencing or by microscopy.

In one embodiment, the method is characterized by the steps of permitting site-specific nicking of chromosomal DNA in a sample by a nicking endonuclease that is tethered to an antibody that is: (i) bound to a target; or (ii) as a secondary antibody, is bound to another antibody that is bound to the target. In one embodiment, the location of a target associated with chromosomal DNA in a sample can be identified by: (a) adding a nicking endonuclease fusion protein (NEFP) comprising the nicking endonuclease and a domain that binds to a constant region of an antibody, wherein the antibody is bound directly or indirectly to a target in a cell; (b) permitting the NEFP to bind to the antibody and preventing NEFP that is not bound to the antibody from binding directly to chromosomal DNA; (c) permitting site specific nicking of the chromosomal DNA in the sample; (d) nick translating the nicked chromosomal DNA with a strand displacing polymerase in the presence of a mixture of dNTPs wherein one or more dNTPs in the mixture is modified for blocking secondary nicking and wherein optionally one or more dNTPs in the mixture is tagged for: (i) permitting visualization of the nicked translated DNA by microscopy; and/or (ii) immobilizing the nicked translated DNA on a matrix; and (e) identifying the location of the target on the DNA.

Examples of samples having chromosomal DNA include eukaryotic cells and bacteria cells. Chromosomal DNA can be distinguished from purified DNA when it is contained in a cell in the form of chromatin or is derived directly from a cell where the target is preferably not disrupted or removed. The cell samples containing the chromosomal DNA may be fixed cells, non-fixed cells or lysates. Examples of a target include, a protein, or a structural feature such as a loop or G-quadruplex or modified nucleotides. Samples may also include viruses or archaea.

Site specific nicking can be achieved using a NEFP in which the nicking endonuclease and the domain that binds to a constant region of the antibody or a target affinity binding moiety are linked by means of a linker peptide. The NEFP may alternatively be a tripartite protein having a nicking endonuclease portion linked indirectly to an antibody binding moiety via a DNA polymerase sandwiched between the nicking endonuclease and the antibody binding moiety. The NEFP for use in the method is capable of being tethered to the target indirectly via an antibody bound to the target or directly by affinity binding through a linked target specific agonist or antagonist to the target.

In an initial step, the fixed or unfixed cells may be made porous to NEFP and antibodies by means of a detergent. The detergent (such as DTT, Triton, Tween or a poloxamer) can increase the porosity of the cell and nuclear membranes thereby allowing access by the composition to the target on the chromosomal DNA in the nucleus.

It may be desirable to raise the temperature of the preparation to above 40° C., above 50° C., above 60° C., above 70° C., above 80° C. or above 90° C. to open up chromatin structure for improved accessibility to the target by the antibody binding target and the NEFP. Antibody that binds to the target may be introduced into the cells. The cells may be bathed, prior to addition of the antibody or after addition of the antibody, in a buffer containing a low concentration of inorganic salt (for example, less than 100 mM salt, preferably less than 55 mM salt) and a glycoaminoglycan (GAG) such as a heparin salt. In these low salt conditions, GAG inhibits binding of NEFP to chromosomal DNA although the NEFP can readily bind to target bound antibody, an affinity binding molecule or the target itself. Once the low salt buffer is replaced with a buffer containing a high concentration of inorganic salt such as NaCl (for example, greater than 400 mM salt preferably at least 1M salt), GAG and unbound NEFP can be washed away and nicking activated by the addition of a magnesium or manganese containing buffer such as NEBuffer™ 2 (New England Biolabs, Ipswich, Mass.).

Site specific nicking of chromosomal DNA in proximity to a target that occurs after a change of buffer is accompanied by polymerase activated nick translation and strand displacement that incorporates into nick sites on the DNA, nucleoside triphosphates (dNTPs) in the reaction mix. In embodiments of the method, one or more of the dNTPs are modified dNTPs: (i) to prevent re-nicking by the nicking endonuclease (for example where the modified nucleotide is a methylated nucleotide); (i) to facilitate immobilization of nick translated fragments through an affinity tag labelled nucleotide (such as biotinylated nucleotide); and/or (iii) to enable visualization by microscopy by means of a dye labelled nucleotide.

Various features may be included in the general method. For example, small fragments are generated by nicking around the position of the target and these fragments may be enriched by immobilization on an affinity substrate enabling the residual chromosomal DNA to be removed by washing. A library can be made from the enriched small fragment DNA followed by sequencing of the DNA fragments and locating the fragments on a genome map.

The methods may utilize a plurality of aliquots derived from a biopsy sample from a multicellular organism such as a human, animal or plant where one aliquot contains the nick translated chromosomal DNA in permeabilized nuclei for visualizing under a microscope and optionally a second aliquot contains the nick translated chromosomal DNA for sequencing.

The methods may be completed at a single temperature and in a single reaction vessel or multiple reaction vessels. A single high temperature step may be desirable to open-up the chromatin structure. This high temperature step may have a duration of 2 hours-12 hours prior to addition of the NEFP and antibodies. For example, a temperature of 40° C., 45° C., 50° C., 55° C., 60° C., 65° C., 70° C., 80° C., 85° C., 90° C. or 100° C.

Uses of embodiments of the method may include identifying and/or locating a target associated with a cancer or with a treatment for a cancer. Advantages of embodiments include the ability to determine the presence of a diagnostic target by microscopy and by sequencing in the same cell or tissue sample from a patient.

Certain features may apply to the methods such as one or more of the following; NEFP that comprises a nicking endonuclease linked to Protein A or Protein G, where the nicking endonuclease in the NEFP may be Nt. CviPII or HNH; the one or more modified dNTPs may be selected from the group consisting of $d^{5m}CTP$, biotinylated CTP and a dye labeled dNTP; one or more modified nucleotides may include a dye labeled dNTP; the chromosomal DNA may be located in a cell that may be an intact living cell, an intact permeabilized nucleus and/or a biopsy sample from a patient; and/or the target may be a protein associated with a cancer or with a treatment for a cancer or with transcriptional regulation of a gene.

In general, kits are provided that contain NEFP and a heparin salt (such as heparin sodium salt) as separate reagents or combined in a single reagent mixture. The NEFP and the heparin may be lyophilized separately or together or may be formulated in a low concentration inorganic salt buffer, in separate compartments or combined in the same compartment. The NEFP may have a sequence that has at least 90% sequence identity to a sequence selected from the group consisting of SEQ ID NOs: 5, 6, 7 and 8.

The kit may further contain in a separate container, a polymerase and one or more modified nucleotides and unmodified nucleotides, such as $d^{5m}CTP$, biotinylated CTP and a dye labeled dNTP and dNTPs. The NEFP in the kit may include a polymerase in a tripartite fusion. The kit may also include separately, magnetic beads coated with an affinity binding molecule for binding at least one of the modified nucleotides and/or a buffer for permeabilizing cells. The kit may further include one or more buffers selected from: a high salt buffer, a low salt buffer and a buffer for activating nicking activity by the nicking endonuclease that contains magnesium ions or manganese ions.

BRIEF DESCRIPTION OF FIGURES

The patent or application file contains at least one drawing executed in color. Copies of this patent or patent application publication with color drawings will be provided by the office upon request and payment of the necessary fee.

FIG. 1A shows a schematic of examples of NEFPs. The Protein A/G-Gamma-HNH (gHNH) is a fusion of the nicking endonuclease gHNH (SEQ ID NO: 4) (also see Zu et al. Nucleic Acids Research, Volume 41, 2013, 378-390) with the Protein A or G at the N-terminal end of the nicking endonuclease via a linker having a sequence: GSATIV (SEQ ID NO:1) for Protein A and GSATGTSAGSTG (SEQ ID NO:2) for Protein G. The C-terminal end of the nicking endonuclease Nt. CviPII (New England Biolabs, Ipswich, Mass.) is fused to Protein A via a linker having the sequence GSGSGS (SEQ ID NO:3). The sequence for gHNH is:

```
                                    (SEQ ID NO: 4)
KKPLRPCCEFHCYNLTRERYCEEHRYKEKETQQDKNRYYD

RFKRDKESTAFYRSKAWERLREQALMRDKGLCLHCKNNR

KIKVADMVDHIIPIKVDPSLKLKLENLQSLCNPCHNRKT

AEDKKKYG.
```

Figure 1A:
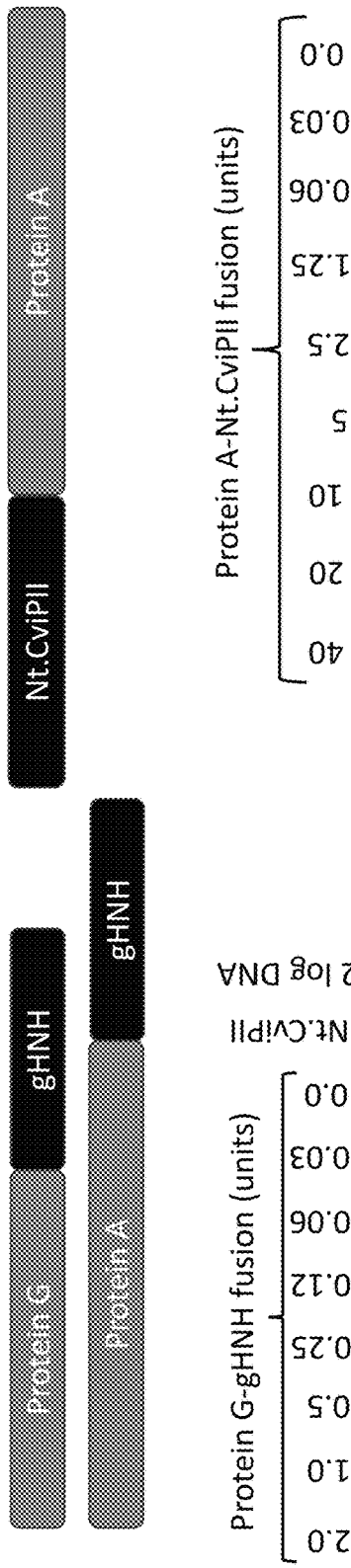
FIG. 1A-1C show that a nicking endonuclease fused to Protein G or Protein A via a linker can nick a DNA substrate as effectively as a nicking endonuclease that is not fused to another protein.
Figure 1C:
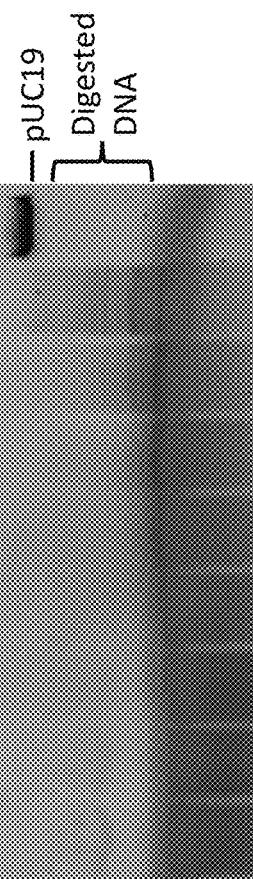
Figure 1B:
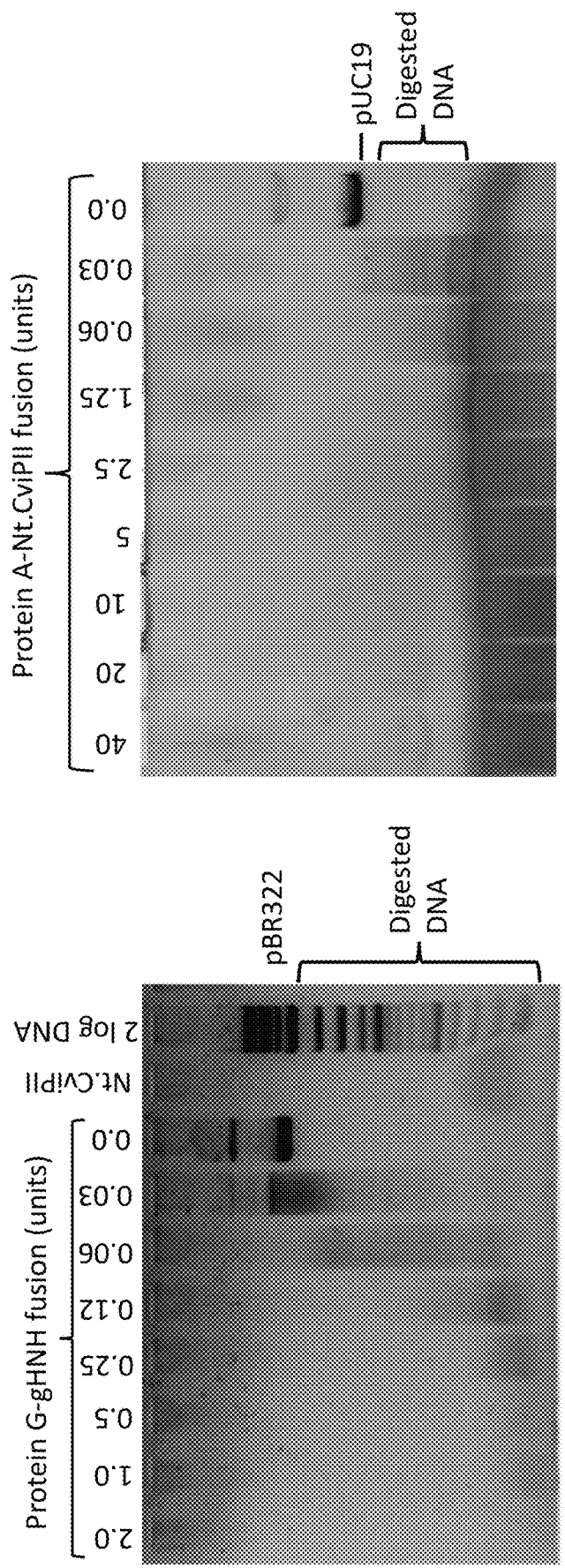

FIG. 1B shows the nicking activity of Protein G-gHNH where the NEFP stock solution (2 units) was diluted in NEBuffer 2 in which magnesium ions were replaced by manganese ions. The nicking activity of Protein G-HNH was compared to a second non-fused nicking endonuclease (Nt.CviPII) (2 units) in the same gel to determine a generalized and consistent cleavage profile and was also compared to a control in the lane labeled 0 containing no nicking endonuclease either fused or unfused.

Complete nicking of 1 μg pBR322 DNA substrate was achieved with 0.25 units of Protein G-gHNH.

FIG. 1C shows the nicking activity of Nt.CviPII-Protein A where a 40 unit stock solution was diluted in NEBuffer 2 (containing magnesium ions required for enzyme activity). The nicking activity was compared to a control in the lane labeled 0 containing no nicking endonuclease either fused or unfused. Complete nicking of 1 μg pBR322 DNA substrate was substantially achieved with 0.06 units of Nt.CviPII-Protein A fusion protein.

FIG. 2A-FIG. 2F shows that heparin Sodium salt inhibits NEFP (Nt.CviPII-Protein A) nicking by negating binding to DNA.

FIG. 2A shows that when heparin was added at an effective concentration to a DNA prior to addition of a NEFP in a low salt (less than 50 mM) NaCl buffer, nicking activity that would otherwise occur was prevented.

From right to left: lane 1 is pUC19, the substrate DNA that was undigested in the absence of any nicking endonuclease.

In lanes 1-9, 2.5 units of NEFP was added to 0.5 μgs of plasmid DNA in the presence of increasing amounts of heparin (0.15-10 mg/ml). Digestion was not observed when 0.3 mg heparin/ml or greater amounts are present.

FIG. 2B shows that when NEFP is added to DNA, it can non-specifically bind to DNA to form a complex with the DNA. Increasing amounts of heparin disrupts complex formation. Nicking activity is prevented by the absence of magnesium ions in the buffer.

From left to right: C is a control that is DNA in the absence of a NEFP or heparin. 0 is a control in which nicking endonuclease was added to DNA in the absence of heparin. The DNA-NEFP complex (DNA-Nt.CviPII-Protein A complex) is seen as a band at the top of the lane. When heparin was added in excess of 4.6 mg/ml, the NEFP is released entirely from the DNA and only the DNA band was observed at the bottom of the gel.

FIG. 2C shows that Protein G (immobilized on magnetic beads) was bound to antibody whether heparin was present or not in the reaction mixture. Heparin did not interfere with this binding. The numbers on the top indicate added heparin quantity in the reaction mgs/ml.

Antibody heavy and light chains that are bound to Protein A/G can be released by boiling and resolved on an SDS gel (B). Any antibody that was free in solution having been eluted or displaced by heparin from Protein A/G could be visualized without boiling (E). The gel shows that in all concentrations of heparin tested, no elution or displacement of antibody occurred.

FIG. 2D is the same as FIG. 2C except Protein A was substituted for Protein G. Here Protein A that was immobilized on beads was shown to bind to antibody in the presence of heparin.

FIG. 2E shows a workflow in which the DNA is not bound to antibody and where Protein A/G-Nicking enzyme complex is not tethered to a DNA binding protein. Instead, any binding in a complex between DNA and the NEFP occurs at the recognition sequence. The results of this workflow are presented in FIG. 2A and FIG. 2B where heparin is shown to inhibit the complex formation.

FIG. 2F shows a workflow used in FIG. 2C and FIG. 2D in which DNA is bound via a DNA binding protein to an antibody and then to the NEFP. In these circumstances the addition of heparin does not disrupt the binding of the NEFP.

Figure 3B:
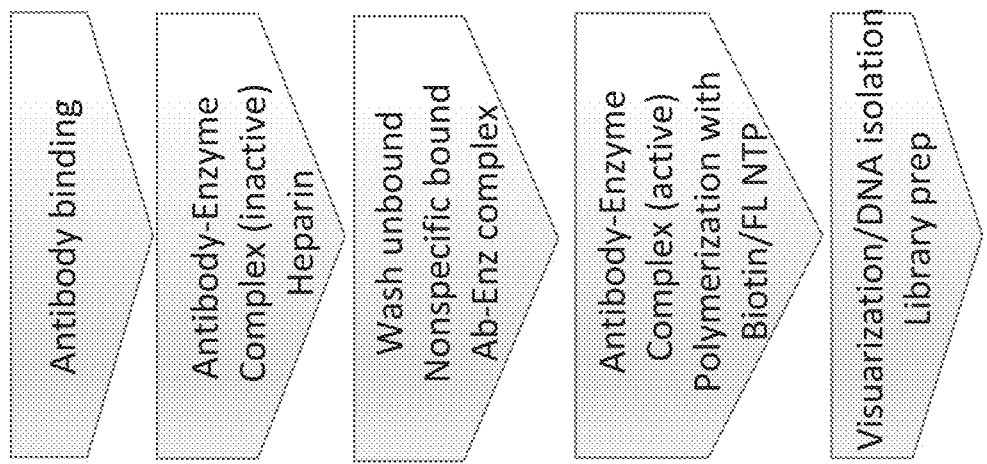
Figure 3A:
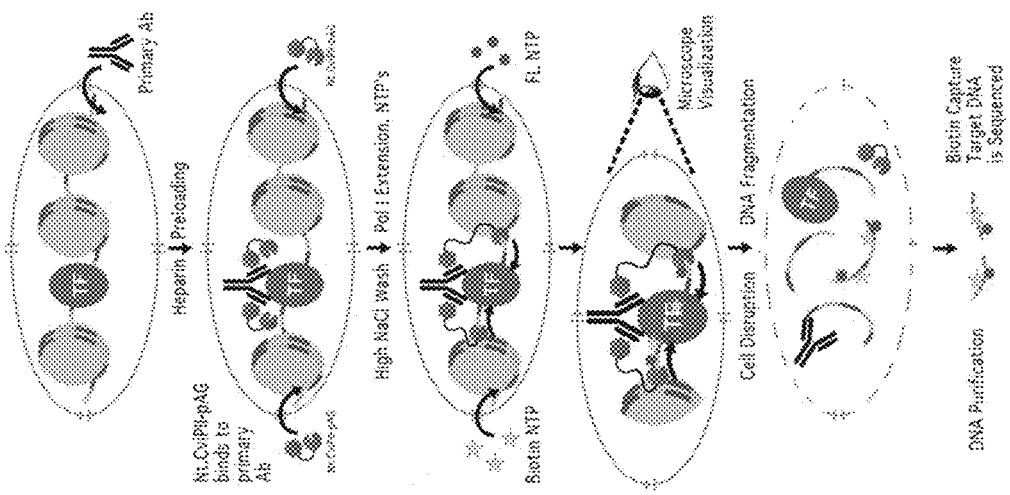

FIG. 3A-FIG. 3B is a workflow showing how the location of DBP can be determined by Nicking Endonuclease Assisted Target Visualization (NEAT-View) and/or sequencing using Nicking Endonuclease Assisted Target Sequencing (NEAT-Seq) methodology.

FIG. 3A shows a schematic that includes: (i) a permeabilized cell nucleus containing a portion of a chromosome with 3 nucleosomes joined by and wrapped around with DNA. A transcription factor (TF) is on the DNA positioned between 2 nucleosomes and an antibody is entering the nucleus to bind the TF; heparin is added in a low <50 mM NaCl buffer; (ii) Nt.CviPII fused to Protein A or Protein G enters the nucleus and binds selectively to the antibody; (iii) after a high salt wash to remove heparin, poll extension with dNTPs and modified dNTPs results in nicking and nick translation from nick sites. Where the modified dNTP contains a fluorescent label, the labeled DNA will be visualized by microscopy; (iv) where the modified dNTP carries a biotin label, the DNA will be released from disrupted cells and immobilized by means of a tag (e.g., Biotin) to affinity bound beads (e.g., streptavidin beads); (v) for purification of the target DNA (TF bound DNA) followed by sequencing.

FIG. 3B is a flow diagram describing a related workflow where the first step is binding of an antibody to the target DNA binding protein followed by treating with a NEFP in the presence of heparin to prevent untethered binding of the NEFP to its recognition sequence, or non-specifically to DNA, and in the absence of metal ions required for nicking activity. The third step indicated is the removal by washing of untethered NEFP. The fourth step is nick translation in the presence of modified nucleotides that include biotin or fluorescent tagged nucleotides and methyl modified nucleotides. The final step shown in this workflow is the visualization of fluorescent tagged target protein by microscopy and/or DNA isolation and library preparation for sequencing.

Figure 4A:
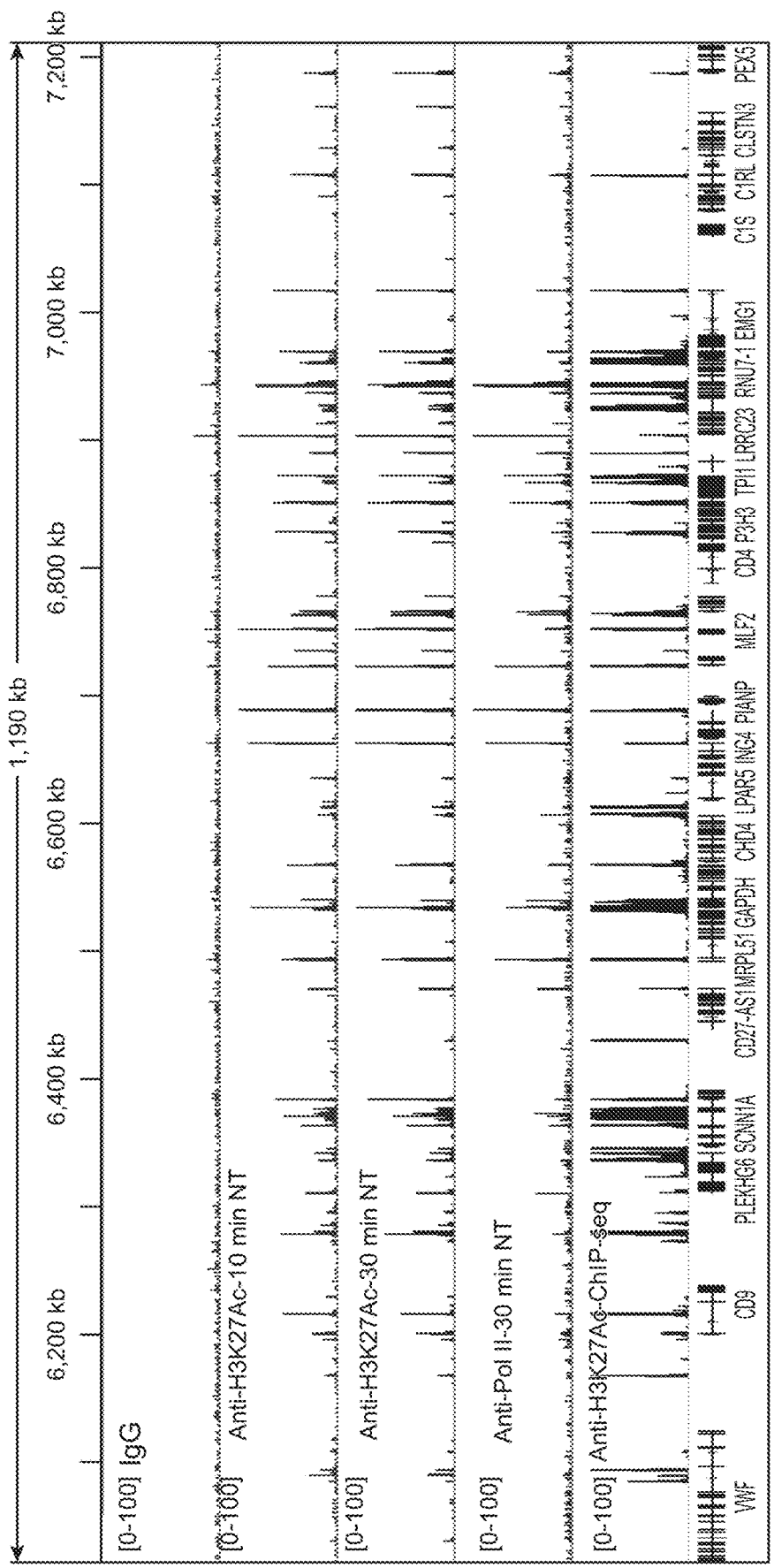
Figure 4B:
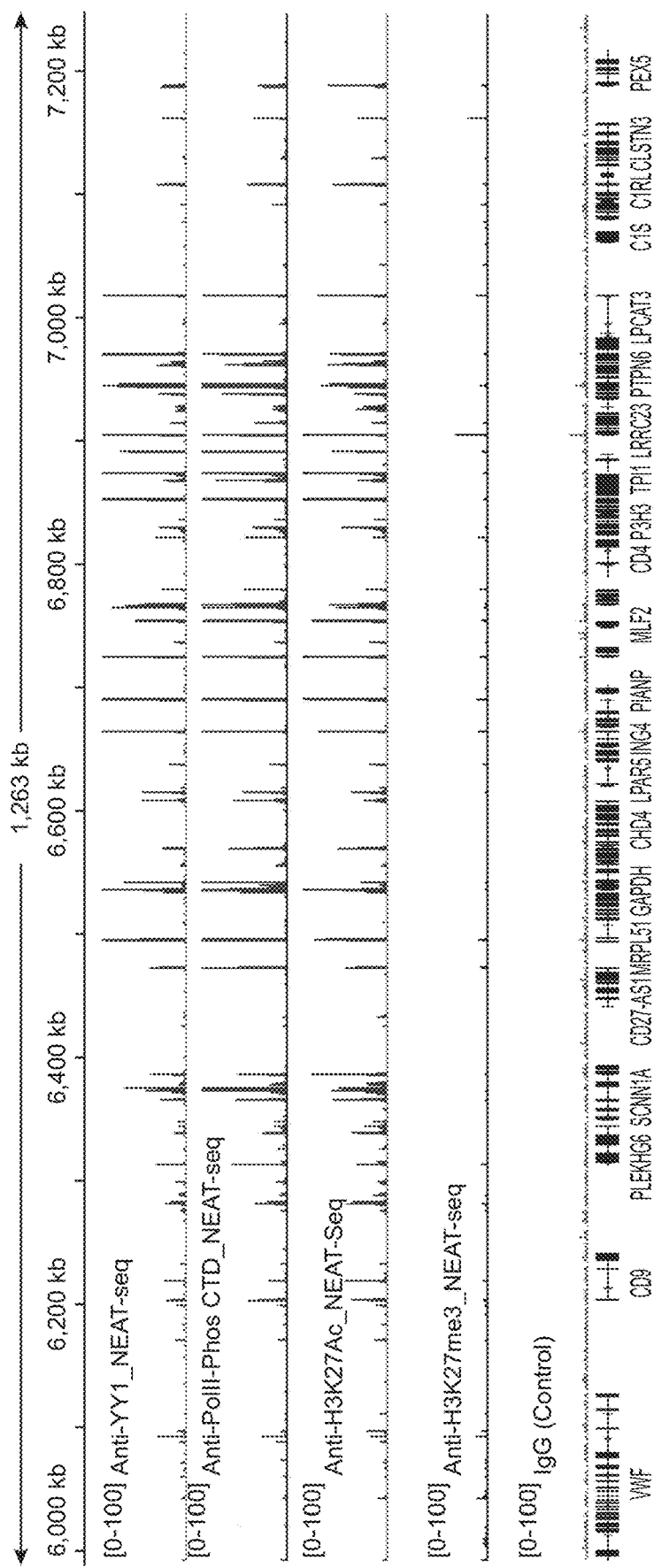
Figure 4C:
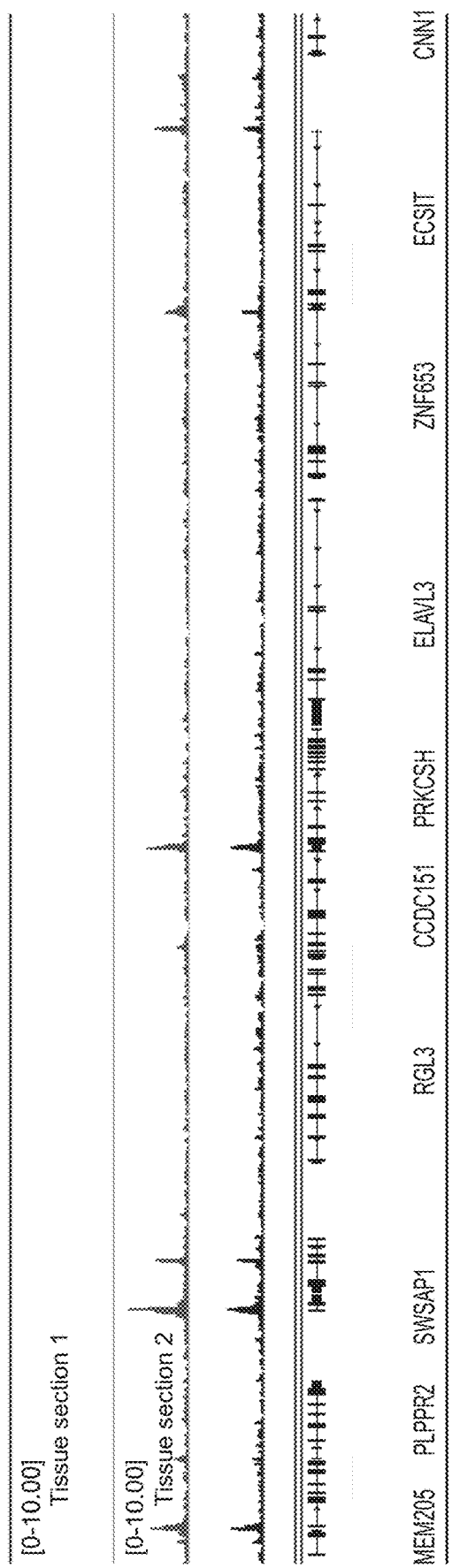

FIG. 4A-FIG. 4C shows an example of NEAT-Seq for identifying the location of the binding sites of Pol II and active histone marks H3K27ac on chromatin (FIG. 4A). The results are compared with those obtained with ChIP-Seq. The results show that NEAT-Seq could be performed with 40 fold less cells than ChIP-seq and provided reproducibly more precise peak locations than ChIP-Seq (250,000 cells versus 10,000,000 cells). Moreover, this was achieved in substantially less time (NEAT-Seq in 1 day versus ChIP-Seq, at least 4 days).

FIG. 4B shows results obtained by NEAT-Seq using 4 different antibodies—Anti-YY1, Anti-PolIII, Anti-H3K27Ac and Anti-H3K27me3 where H3K27Ac is an active histone mark and H3K27me3 is an inactive mark on chromatin.

FIG. 4C shows results obtained using NEAT-Seq on 5-10 micron thickness human liver FFPE sections using anti-H3K27Ac antibody.

Figure 5:
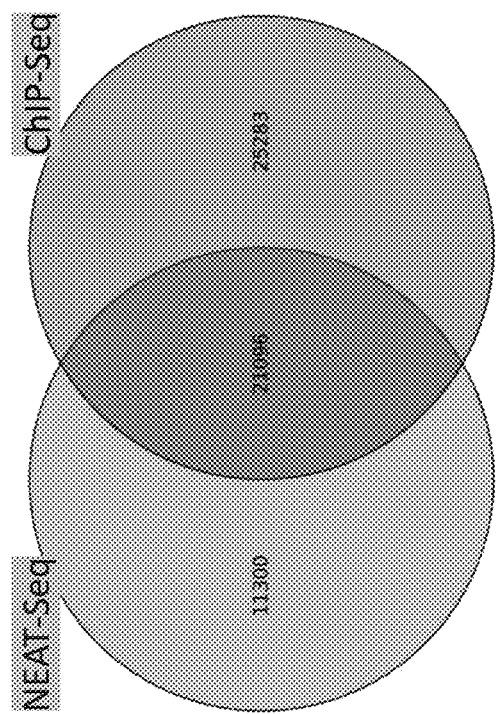

FIG. 5 provides a quantitative view of common binding sites for H3K27ac on chromatin comparing ChIP-Seq with NEAT-Seq in a Venn diagram that displays a much higher background count for ChIP-seq than for NEAT-Seq.

FIG. 6A-FIG. 6B shows that a tripartite Protein A-DNA Polymerase nicking enzyme fusion can replace Nt.CViPII Protein A/G in the workflows shown in FIG. 3A-FIG. 3B.

FIG. 6A shows a schematic of a NEFP having three functional components including a nicking component, a polymerase component, and Protein A/G.

FIG. 6B shows an experimental design in which heparin is introduced to prevent nicking and polymerase activity from the untethered tripartite fusion protein. The tripartite fusion may be particularly useful in circumstances where the DNA is fragmented as a result of formalin fixation of cell samples. The nicked DNA is a negative control where no antigen (Ag) is present on the DNA for binding antibody (Ab). In contrast, the presence of the antigen results in nick translation and incorporation of one or more modified nucleotides.

Figure 7A:
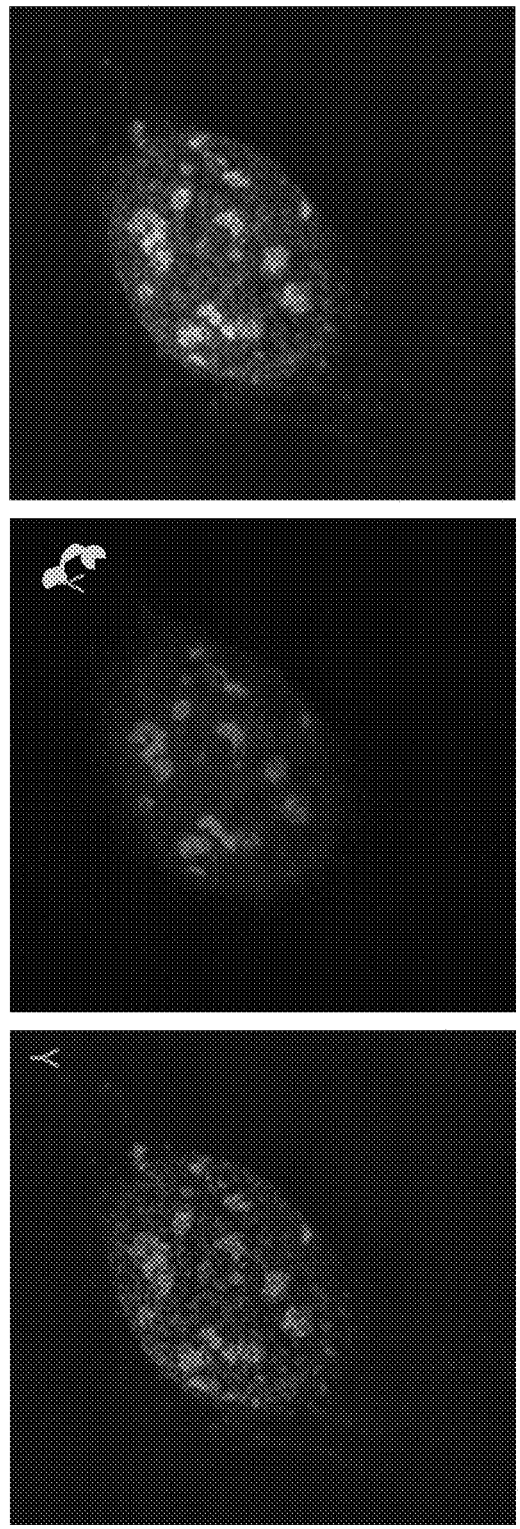

FIG. 7A-7B shows the location of two different proteins, each by means of three views of a cell nucleus.

FIG. 7A shows from left to right: HP1 alpha (heterochromatin protein) that was located throughout the cell genome probed with antibody (Anti-HPI) and a secondary antibody conjugated with Alexa 488 fluorophore, HPI alpha bound DNA targeted and incorporated with Texas-Red conjugated dATP using Nicking Enzyme (Endonuclease) Assisted Target Viewing (NEAT-View), and a merged view of the previous two localization.

FIG. 7B shows from left to right, nucleolar phosphoprotein B23 compartmentalized in the nucleolus only probed with antibody (Anti-NPMI), B23 bound DNA targeted and incorporated with Texas-Red conjugated dATP using NEAT-View; and the superimposition of HPI staining and NEAT-View staining.

Figure 8:
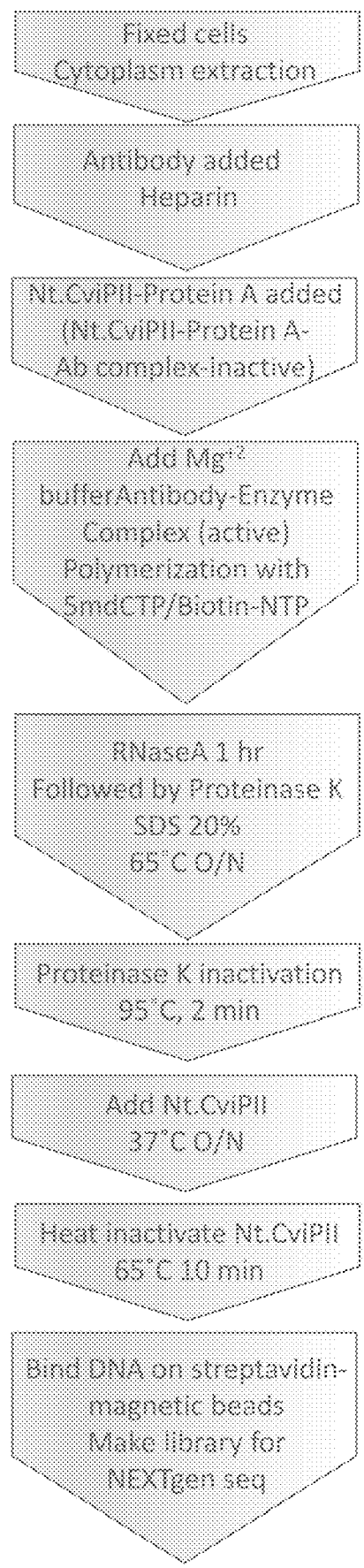

FIG. 8 provides a workflow for a one tube method for NEAT-Seq. In the first step, cytoplasmic extraction leaves nuclei in a fixed cell sample. Antibody that targets the DNA binding protein of interest is added to the nuclei along with heparin in a low NaCl buffer (<100 mM). Excess NEFP is added in a buffer that lacks the metal ions required for activity and becomes tethered to the antibody that has bound the DNA binding protein. Heparin is removed along with untethered excess NEFP by washing in 1M Nacl buffer (>400 mM). Polymerase and dNTPs including modified dNTPs (e.g., $^{5m}$dCTP/Biotin labeled dNTP) are added to the sample in a buffer containing the metal ions in low NaCl buffer (<100 mM) to activate nicking. The nuclei are then treated with Proteinase K (New England Biolabs, Ipswich, Mass.) and RNase to remove nuclear protein and RNA. Untethered nicking endonuclease is added to degrade the DNA that is not already nick translated and containing $^{5m}$CTP, leaving only small fragments of DNA of interest. These fragments are immobilized, purified, and then sequenced.

Figure 9:
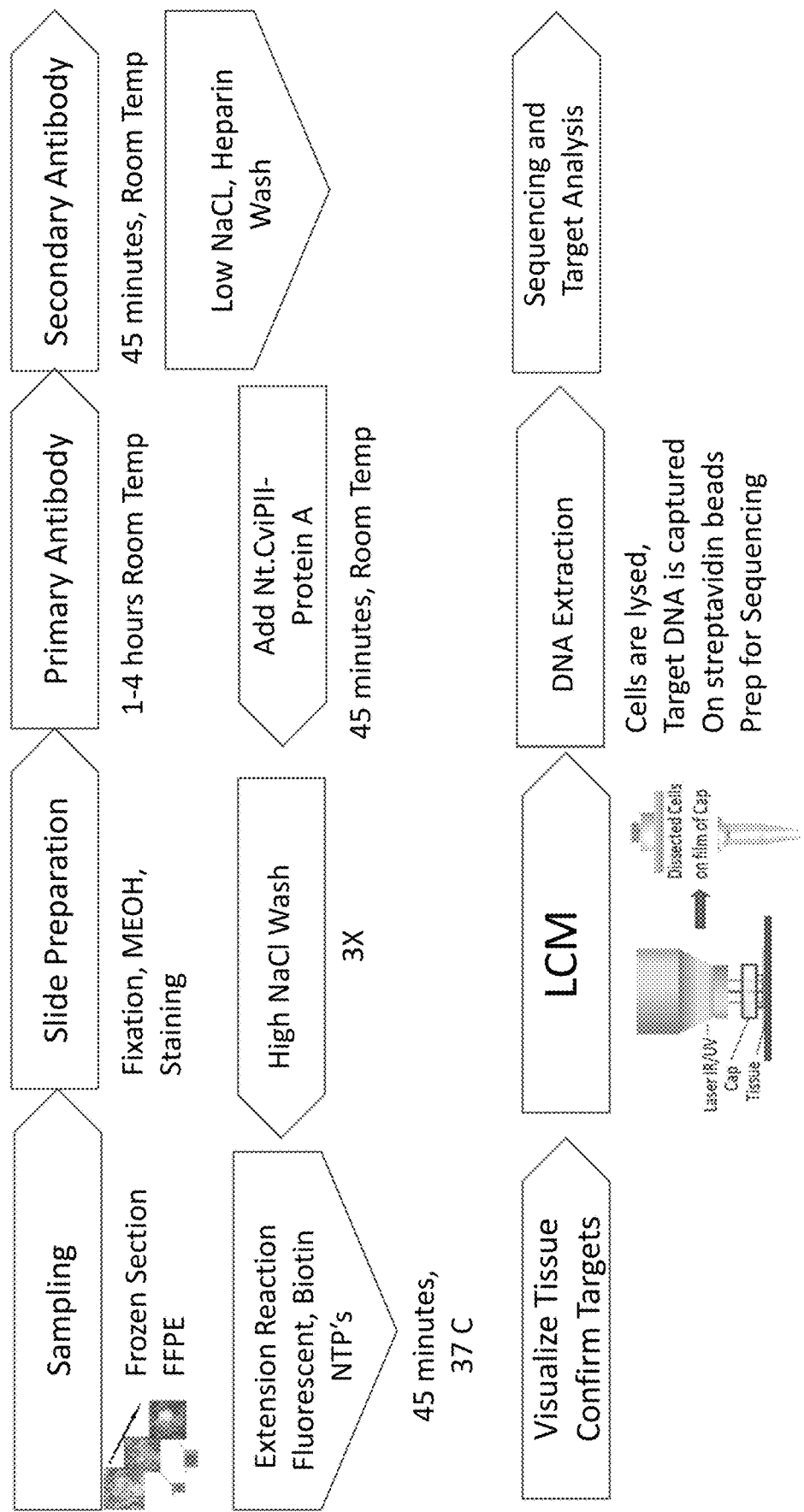

FIG. 9 shows a workflow for both NEAT-View and NEAT-Seq using laser capture microdissection (LCM). The same sample can be visually analyzed under a microscope and sequenced. The cell sample can be a frozen section or an FFPE sample. The cells can be fixed and then treated with a primary antibody. The signal can be amplified if a secondary antibody is used to enhance the signal from a rarely occurring target. A low salt wash removes excess antibody prior to the addition of heparin and an excess of NEFP to the cells. A high salt wash removes excess NEFP prior to addition of a polymerase and dNTPs as described above. The tissue can then be visualized as shown in FIG. 7A-7C. A portion of the cells can be obtained for example by LCM (see for example, Thermo Fisher Scientific, Waltham, Mass.), followed by DNA extraction and sequencing.

FIG. 10A-10F shows a schematic for NEAT-Seq also shown in FIG. 3A-3B and FIG. 8 for comparison with antibody multiplexing shown in FIG. 11A-11G.

FIG. 10A shows a tagged primary antibody binding to a DNA binding protein, in this case, a transcription factor. Here the chromatin is open around the binding protein and nucleosomes are shown upstream and downstream of the transcription factor. FIG. 10B shows the introduction of a fusion protein that is a nicking enzyme (e.g., Nt.CviPII) fused to an antibody binding moiety (e.g., Protein A). A small molecule inhibitor of the nicking enzyme (e.g., heparin) is shown binding to the nicking enzyme before and after binding of the Protein A. FIG. 10C shows the removal of heparin after a change in buffer from buffer 1 to buffer 2 and activation of nicking by the Protein A tethered Nt. CviPII. FIG. 10D shows the strand displacement amplification that occurs in the presence of a DNA polymerase (e.g., DNA polymerase I contained in buffer 2). If an affinity tag such as biotin or a detectable label such as a fluorescent labelled dNTP or both are added with the polymerase, the DNA around the nick will be so labelled. If the tag is biotin, this facilitates enrichment of DNA fragments for sequencing after FIGS. 10E and 10F. If the label is fluorescent, this facilitates microscope dependent visualization of the DNA protein binding site. Both labels may be used in the same reaction for both sequencing and microscopic visualization. FIG. 10E shows the step of nuclear membrane disruption for release of total DNA both cleaved and genomic. FIG. 10F shows the enriched labelled and tagged DNA fragment products.

FIG. 11A-11G shows an embodiment of a method for signal amplification of rare events involving DBP that may be indicators of pathogenicity.

FIGS. 11A and 11B show the addition of a primary antibody that recognizes and binds to the DNA binding protein and a secondary antibody that binds to the primary antibody where the secondary antibody contains a label and/or tag. FIG. 11C-11G proceed according to the steps outlined in FIG. 10B-10F.

FIG. 12A-12E shows various alternative embodiments of the method in FIG. 10A-10B and FIG. 11A-11B.

FIG. 12A shows the binding of a primary antibody to a DNA binding protein (e.g., DNA (cytosine-5)-methyltransferase 1 (DNMT1) via an antagonist to DNMT1 illustrated here by S-Adenosyl-L-homocysteine (SAH).

FIG. 12B shows how a fusion between the nicking enzyme and an affinity protein or peptide of the DNA binding protein is an alternative approach to NEAT-Seq.

FIG. 12C shows a primary antibody may be used to identify a particular DNA structure such as a loop or a G-quadruplex in chromosomal DNA. The G-quadruplex is a feature of gene regulation and therefore of significance in diagnostic tests. Once the antibody is bound, the method can proceed as illustrated above.

FIG. 12D shows a primary antibody may be used to identify a modified nucleotide in chromosomal DNA. The presence of modified nucleotides is a feature of gene regulation and therefore of significance in diagnostic tests. Once the antibody is bound, the method can proceed as illustrated above.

FIG. 12E shows a primary antibody may be used to identify chemical crosslinking that is a feature of DNA damage in chromosomal DNA. Once the antibody is bound, the method can proceed as illustrated above.

Figure 13:
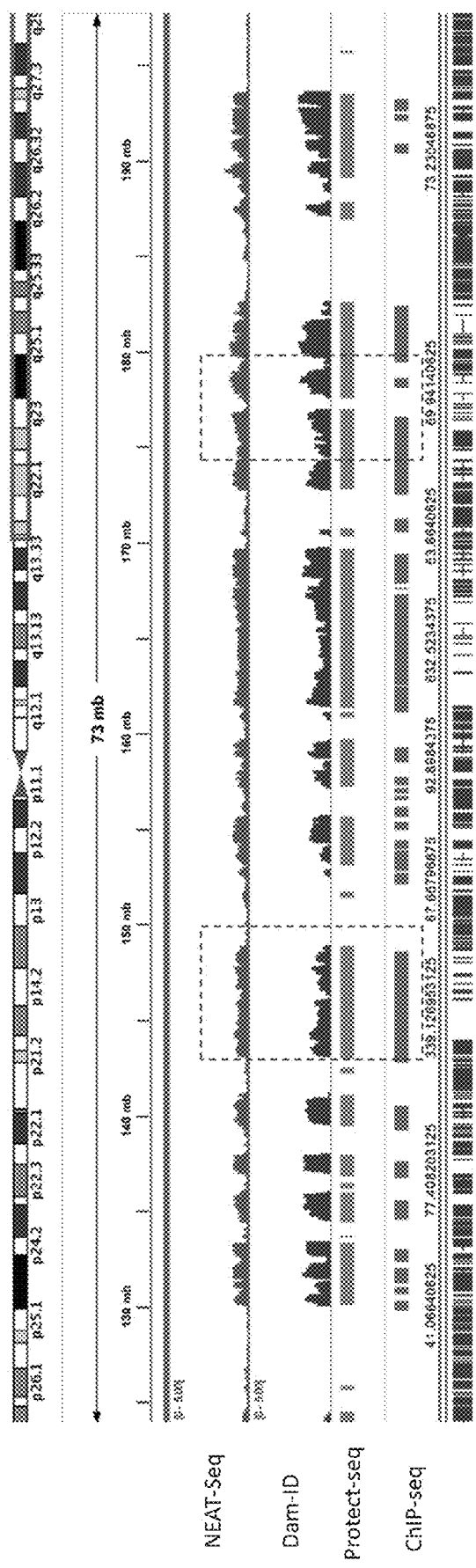

FIG. 13 shows a comparison between results obtained using the NEAT-Seq method as described in Example 3 and prior art methods, namely, Dam-ID (accession number: 4DNFIFKMR1J8), Protect-Seq (accession number: GSE135580) and ChIP-Seq (accession number: GSE57149) (see Dekker, et al. Nature 549, 219-226 (2017), van Schaik, et al. (2020) EMBO reports, 21(11), e50636; Lund, et al. Nucleus 2015; 6(1):30-9; and Spracklin, et al. (2020). Nucleic acids research, 48(3), e16).

Dotted boxes show representative lamin associated domain detected by using all different methods. For the broad peak calling "-broad" option was used. NEAT-Seq of Lamin B2 was performed on 2% formaldehyde or methanol fixed cells.

All methods resulted in identifying the lamin associated domains (LAD) on chromosome 3 between 13.33 and 27.3 on one arm of the chromosome and P26.1-p11.1 on the second arm of the chromosome. A map of the chromosome 3 is shown in the top line above the read data.

NEAT-Seq map is shown in the first row of reads for MCF7 breast cancer cells. Dam-ID-seq map is shown in the second row of reads for HCT116 cells; Protect-Seq map is shown in the third row of reads for HCT116 cells; and Chip-Seq map is shown in the fourth row of reads for HeLa cells. The line at the bottom of the figure denotes the location of genes in the chromosome section. All the cells analyzed have lamin in the nuclear membrane that binds to the chromocenter of the chromosomes in resting cells. A significant benefit of NEAT-Seq is that the results are obtained with fewer cells compared to the other methods and completed in shorter times. Dam-ID used $10^6$ HCT116 cells, Chip-Seq used $10^7$ HeLa cells, Protect-Seq used $10^7$ HCT116 cells, whereas NEAT-Seq used $5\text{-}10\times10^4$ MCF7 breast cancer cells.

Figure 14C:
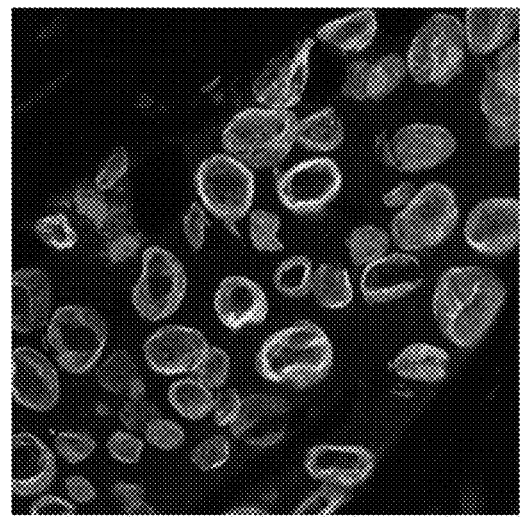
Figure 14B:
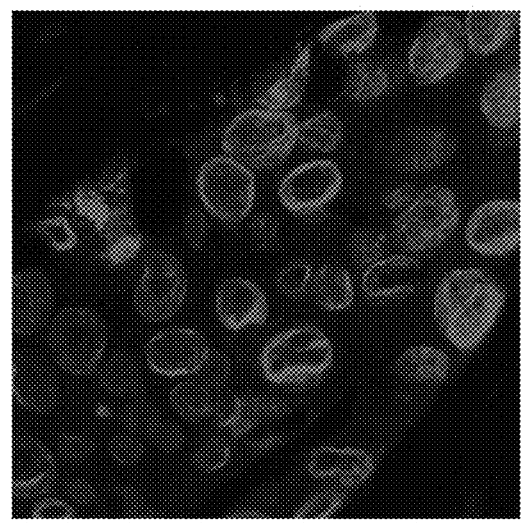
Figure 14A:
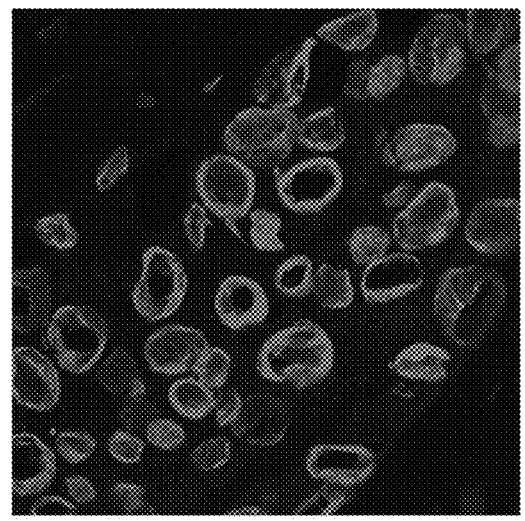

FIG. 14A-14C shows that there is a reduced occurrence of Lamin in chromosomes from a 5-10 µM breast cancer tissue section by microscopy of marker stained cells using NEAT-View. Tissue section was fixed with methanol.

FIG. 14A shows Lamin B2 compartmentalized in the nucleus only when probed with anti-lamin B2 antibody to localize the protein. This creates a green, fluorescent signal that corresponds to the location of the protein;

FIG. 14B shows Lamin bound DNA targeted and incorporated with Texas-Red conjugated dATP using NEAT-View; and FIG. 14C shows the superimposition of Lamin B2 antibody staining and NEAT-View staining wherein the coincidence of the anti-lamin B2 antibody and the bound DNA results in a yellow color that can be visualized by microscopy.

FIG. 15A-15F shows an example of Lamin B2 bound to nuclear DNA in a MCF7 breast cancer cell line and analysis of lamin bound domain in various human cell lines.

FIG. 15A shows a methanol fixed MCF7 breast cancer cells are probed with anti-Lamin B2 antibody to reveal lamin associated domains at the nuclear membrane, that can be detected by a green coloration.

FIG. 15B shows NEAT-View reaction using the bound lamin antibody and Protein A fused Nt.CviPII in the presence of TexasRed-dATP and biotinylated dCTP, as detected by a red coloration to demonstrate nucleotide incorporation/ extension reaction.

FIG. 15C shows the merge of both A and B to demonstrate colocalization detectable by yellow.

FIG. 15D shows comparison of other lamin associated domain analysis with NEAT-Seq using a Venn diagram to show common and unique peak between NEAT-Seq, peaks called from different datasets. Dam-ID (HCT116 cell line; accession number 4DNFIFKMR1J8); Protect-Seq (HCT116 cells; accession number GSE135580); and ChIP-seq (HeLa cell line; accession number GSE57149). All common LAD domains are indicated.

FIG. 15E shows the total number of peaks obtained in NEAT-Seq, Dam-ID, Protect-Seq and ChIP-Seq.

FIG. 15F shows common lamin associated domains percentage between different methods.

DETAILED DESCRIPTION OF EMBODIMENTS

A feature of both NEAT-Seq and NEAT-View is to indirectly or directly tether a nicking endonuclease to a target on chromosomal DNA. Once tethered, the nicking activity of the nicking endonuclease is activated and DNA is nicked in the 3-dimensional space proximal to the target where the tethered nicking endonucleases is capable of nicking DNA at recognition sequences within its reach. The use of tethered nicking endonucleases enables nick translation from nick sites between two nucleosomes or until another protein bound to the chromosomal DNA is encountered by the polymerase. Nick translation by means of a strand displacing polymerase follows with dNTPs in the reaction mix. Some of the dNTPs are modified so that when integrated in the nick translated DNA, the modified bases block further nicking by the nicking endonuclease. An example of a modified base that blocks nicking is $^{5m}C$. This single cycle of nick translation permits the incorporation of modified nucleotides, some of which may include tags.

Other dNTPs may also be used in the reaction mixture that contain tags to facilitate immobilization and/or visualization by microscopy.

A feature of NEAT-Seq is to immobilize only those DNA fragments that have been nick translated by means of a tag such as biotin on some of the dNTPs. If the nucleotides provided for nick translation include a modified nucleotide that is tagged with an affinity tag such as biotin, then the nick translated DNA can be easily separated after cell lysis from the rest of the nuclear DNA in the presence of an affinity binding substrate such as streptavidin coated magnetic beads. The immobilized fragments are then made into a library and sequenced. This provides a means of accurately identifying the DNA bound and in close proximity, and including a target, to provide architectural context. The efficiency of mapping the target protein is greater using this approach than can be achieved using methods that rely on double stranded cleavage of DNA for diffusion through the nuclear membrane. This benefit can lead to a reduction in the amount of starting material as well as localization of the protein in 3-dimensional context. Embodiments of the method require less than 10,000 cells more particularly less than 1000 cells, more particularly, for example, less than 250 cells or 100 cells to provide the diagnostic data required to determine the presence and location of target proteins indicative of disease. Once the nick translated DNA has been immobilized and separated from the rest of the DNA, it can be sequenced and mapped.

In NEAT-View, some of the dNTPs are linked to dyes or fluorescent tags so that the presence and location can be detected by microscopy. NEAT-Seq and NEAT-View can be performed on the same samples as shown in FIG. 9 or on different aliquots of the same samples where NEAT View and NEAT-seq are performed in parallel. Mapping by sequencing of the cleaved DNA fragments or by microscopy provides information about the number and type of genomic interactions of the target.

Both NEAT-Seq and NEAT-View include the use of a sequence specific DNA nicking enzyme such as a nicking endonuclease that has been fused to an antibody binding moiety such as Protein A, Protein G and/or Protein L or other affinity binding moiety. Protein A, Protein L, and Protein G or a combination of more than one of the above moieties in tandem can be used in NEFP. Moieties in tandem can create strong binder that will enable removal of non-specific DNA binding NEFP to be treated more stringently to reduce the background. The antibody binding moiety may be a fusion of a plurality of two or more different protein selected from Protein A, Protein G and Protein L or peptide fragments thereof (for tandem linkage of Protein L and G as an affinity reagent see U.S. Pat. No. 5,965,390). Examples of the use of two different fusion moieties are shown in FIG. 1A. Additionally, the nicking endonuclease may be fused to a polymerase to form a tripartite fusion protein. An example is shown in FIG. 6A. The fusion protein is referred to here as the NEFP. The managed nick translation enables both the integration of labeled modified nucleotides that can be used for direct visualization of the target and/or tags used for separating the cleaved fragments adjacent to the target from the rest of the chromosomal DNA and thereby mapping the location of the target.

The NEFP may be added to unfixed, fresh or frozen cells or to fixed cells either before, after or at the same time as antigen specific antibodies that bind a target on chromosomal DNA (see examples of different types of target in FIG. 12A-12E).

Non-specific binding of NEFP to DNA in the absence of Mg or Mn ions is a strong interaction that is very difficult to reverse even in high NaCl and detergents. A feature of embodiments of the method that has resulted in the enhancement of its efficacy is the inhibition of this interaction between a NEFP and DNA at non-specific noncanonical sequences by the addition to a low salt buffer containing a GAG. An example of a suitable GAG is an acidic GAG such as a non-sulfated acidic GAG, such as heparin such as a heparin salt. While not wishing to be limited by theory, it is proposed that the inhibition effect of GAG in low salt occurs under conditions that neutralize charge of the nicking endonuclease at neutral pH to prevent its binding to the negatively charged DNA. A feature of heparin is that its structure resembles the backbone of DNA. GAG prevents the NEFP from binding to DNA and therefore prevents nicking in low ionic (inorganic) salt concentrations. The ionic or inorganic salt described herein includes a salt having a cation selected from potassium, sodium, lithium and calcium and an anion selected from chlorine or bromine. The low salt conditions includes a molar concentration of less than 110 mM salt. In a further example, the low salt concentration may be no more than 75 mM or no more than 50 mM NaCl.

The inhibitory effect on the NEFP is reversed by changing the salt conditions to a high salt concentration where the high concentration salt is an inorganic (ionic) salt that may be the same or optionally different from the salt in the low salt buffer. A high salt concentration refers to a concentration of 400 mM to 2 M salt such as for example, a high salt that is at least 400 mM NaCl, for example, a high salt concentration that is greater than 700 mM NaCl, for example a high salt concentration that is at least 1 M NaCl.

The low salt concentration suitable for binding a nicking endonuclease to heparin, and a high salt concentration for removal of the heparin from the nicking endonuclease may vary according to the particular nicking endonuclease. For example, for Nt.CviPII, the binding of heparin salt to the NEFP occurs at salt concentrations below 100 mM NaCl and elution occurs at high salt concentrations of above 400 mM NaCl.

The inhibition of binding of NEFP to DNA in the presence of GAG as described above enables high concentrations of NEFP to be added to cells to detect the very small amounts of the target on chromosomal DNA without creating unacceptable background signals from non-specific DNA binding or nicking. Consequently, embodiments of the method include inhibiting the DNA binding site of the NEFP with a reversible inhibitor before the nicking endonuclease moiety in the NEFP can interact with the chromosomal DNA.

An excess concentration of NEFP relative to the antibody bound target ensures complete saturation of the target with the bound nicking endonuclease enabling rarely occurring targets in a genomic DNA to be detected. In addition, excess concentration of NEFP enables shorter incubation times. After binding to the target specific antibody, excess unbound NEFP is removed in high NaCl buffer and the endonuclease cleavage activity is activated in a low NaCl buffer containing magnesium or manganese ions.

In one embodiment, the NEFP and heparin salt are added to cells or tissue sections in which the cytoplasmic and nuclear membranes have been permealized by detergent (e.g., Tween and/or Triton). These cells or tissue samples are preferentially flooded with heparin salt in a low salt buffer prior to the addition of the NEFP, itself preferentially in a heparin salt buffer. This ensures that NEFP is always in contact with heparin as the binding component of the NEFP (e.g., Nt.CviPII fused to Protein A or G+L moiety) find the antibody target. After a short incubation, in which the Nt.CviPII-Protein G+L or Nt.CviPII-Protein A finds the antibody target, a 1 M NaCl$_2$ wash removes the heparin from the active site of Nt.CviPII, and any excess nicking complex that had not bound to the antibody. The high salt wash is removed and replaced with a low salt buffer containing magnesium or manganese ions rendering the enzyme competent to initiate a DNA nick near the site of the antibody. Further details of this embodiment are provided in Example 9.

An alternative or additional option to a GAG such as heparin salt is an aptamer that would reversibly bind to the nicking endonuclease so that under low salt conditions, the aptamer would bind but would be released under high salt conditions.

In certain embodiments, a heat step may be introduced into the method to open up the chromosomal DNA to binding of antibody to target. The temperature may be raised up to 70° C., 80° C., 90° C. or 100° C. for this purpose for up to 30 minutes, 40 minutes, 50 minutes or 60 minutes at the same time or shortly after the antibody is added to the nuclei. In other embodiments, the method can be performed at substantially the same temperature.

In embodiments of the method, unbound antibody directed to a target (for example, a protein such as a transcription factor or histone protein or a structural modification such as an R-loop or quadruplex) can be removed by washing before adding an excess of the NEFP. Heparin (e.g., heparin sodium salt) may be added to the reaction before during or after the addition of the NEFP. In the absence of metal ions, neither antibody-bound nor unbound nicking endonucleases such as Nt.CviPII or gHNH will cleave DNA. A low salt buffer containing manganese or magnesium ions is added after removal of unbound NEFP and heparin in a high salt buffer to initiate nicking activity.

Examples of NEFPs are provided below:

NEFP: Protein G-linker-gHNH nicking endonuclease:
(SEQ ID NO: 5)
MKGETTTEAVDAATAEKVFKQYANDNGVDGEWTYDDATKT

FTVTEKPEVIDASELTPAVTTYKLVINGKTLKGETTTEAV

DAATAEKVFKQYANDNGVDGEWTYDDATKTFTVTEKPEVI

DASELTPAVTTYKLVINGKTLKGETTTKAVDAETAEKAFK

QYANDNGVDGVWTYDDATKTFTVTE<u>GSATIV</u>KKPLRPCCE

FHCYNLTRERYCEEHRYKEKETQQDKNRYYDRFKRDKEST

-continued

AFYRSKAWERLREQALMRDKGLCLHCKNNRKIKVADMVDH

IIPIKVDPSLKLKLENLQSLCNPCHNRKTAEDKKKYG

NEFP: Protein A-linker-gHNH nicking endonuclease:
(SEQ ID NO: 6)
AAQHDEAQQNAFYQVLNMPNLNADQRNGFIQSLKDDPSQS

ANVLGEAQKLNDSQAPKADAQQNKFNKDQQSAFYEILNMP

NLNEEQRNGFIQSLKDDPSQSTNVLGEAKKLNESQAPKAD

NNFNKEQQNAFYEILNMPNLNEEQRNGFIQSLKDDPSQSA

NLLAEAKKLNDAQAPKADNKFNKEQQNAFYEILHLPNLTE

EQRNGFIQSLKDDPSVSKEILAEAKKLNDAQAPKE<u>GSATG</u>

<u>TSAGSTG</u>KKPLRPCCEFHCYNLTRERYCEEHRYKEKETQQ

DKNRYYDRFKRDKESTAFYRSKAWERLREQALMRDKGLCL

HCKNNRKIKVADMVDHIIPIKVDPSLKLKLENLQSLCNPC

HNRKTAEDKKKYG

NEFP: Protein G-linker-Nt.CviPII nicking endonuclease:
(SEQ ID NO: 7)
MKGETTTEAVDAATAEKVFKQYANDNGVDGEWTYDDATKT

FTVTEKPEVIDASELTPAVTTYKLVINGKTLKGETTTEAV

DAATAEKVFKQYANDNGVDGEWTYDDATKTFTVTEKPEVI

DASELTPAVTTYKLVINGKTLKGETTTKAVDAETAEKAFK

QYANDNGVDGVWTYDDATKTFTVTE<u>GSATIV</u>MYIYMSTPQ

AKTKYYEQRFVNDFYKELERNKVSLPVTIVLKDNLGIKQV

IQNGSGVRVLRDKANAKSPSKIKSEELGRHVTSKADIALF

TEEKNGTKVDVAWISPQSHKDFLGKKITPAQYFDASSDVM

FKTKIGQPKEIKELKNKMISLSVPLTATKYCWPKYKSGTS

LRIWDDVQSTILMNMAIFGVEFGKAYCRNNANILMVGDP

LIEVKDDKTIILTTKENGFSLANGFAEYIPSKDKPIFFTK

PTSGKKTVVDGKTIEGVSVWIIYRSYAGSKNRKIDDVLKN

KIELISSSCSVKKKDNFVSIMQSKKITSPPKSKKITSPPK

SKKITSPSKSKKITNFFMKK

NEFP: Protein A-linker-Nt.CviPII nicking endonuclease:
(SEQ ID NO: 8)
AAQHDEAQQNAFYQVLNMPNLNADQRNGFIQSLKDDPSQS

ANVLGEAQKLNDSQAPKADAQQNKFNKDQQSAFYEILNMP

NLNEEQRNGFIQSLKDDPSQSTNVLGEAKKLNESQAPKAD

NNFNKEQQNAFYEILNMPNLNEEQRNGFIQSLKDDPSQSA

NLLAEAKKLNDAQAPKADNKFNKEQQNAFYEILHLPNLTE

EQRNGFIQSLKDDPSVSKEILAEAKKLNDAQAPKE<u>GSATG</u>

<u>TSAGSTG</u>MYIYMSTPQAKTKYYEQRFVNDFYKELERNKVS

LPVTIVLKDNLGIKQVIQNGSGVRVLRDKANAKSPSKIKS

EELGRHVTSKADIALFTEEKNGTKVDVAWISPQSHKDFLG

KKITPAQYFDASSDVMFKTKIGQPKEIKELKNKMISLSV

-continued

```
PLTATKYCWPKYKSGTSLRIWDDVQSTILMNMAIFGVEFG

KAYCRNNANILMVGDPLIEVKDDKTIILTTKENGFSLANG

FAEYIPSKDKPIFFTKPTSGKKTVVDGKTIEGVSVWIIYR

SYAGSKNRKIDDVLKNKIELISSSCSVKKKDNFVSIMQSK

KITSPPKSKKITSPPKSKKITSPSKSKKITNFFMKK
```

Manganese ions have the added benefit of loosening the sequence specificity of the nicking endonucleases. Either magnesium or manganese ions are also present in the reaction buffer containing polymerase and dNTPs to enable nick translation to occur.

The use of a nicking endonuclease as a single strand cleavage enzyme for facilitating nick translation has advantages over methods that rely on DNases for double stranded DNA cleavage in methods that are directed to mapping DBP. DNases, e.g., micrococcal nuclease, and DNase I are non-specific cleavage enzymes that cleave and progressively degrade double stranded and single stranded DNA and RNA to mononucleotides. Hence not only must the amount of DNase be titrated, but the reactions should be conducted on ice to limit cleavage. The presence of any excess DNases at the time calcium ions are added to activate DNase is likely to result in high levels of background. In contrast, nicking endonucleases are sequence specific and can be added in excess. No titration is required, and the cleavage reaction can be performed at room temperature or 37° C. Moreover, the capture of released DNA fragments for sequencing from embodiments of the present method does not rely on permeation of the DNA out of the nucleus and/or cytoplasm as required by the "cut and run" method (see for example U.S. Pat. No. 7,790,379, also Schmid, et al. Mol Cell. 2004 Oct. 8; 16(1):147-57). It is envisaged that with the use of heparin as described herein, DNases although not as desirable as nicking endonucleases might under certain conditions be utilized in the present methods. Features of components and steps of the methods and compositions are provided below.

Nicking Endonucleases

A nicking endonuclease is generally a modified or naturally occurring restriction endonuclease that preferentially cleaves only one strand in a DNA duplex at or proximal to a recognition sequence. Restriction endonucleases including nicking endonucleases differ from DNases because restriction endonucleases recognize specific sequences and then cleave in a sequence dependent manner. The use of nicking endonucleases in various reactions is provided in US 2019/0153435. This reference details nicking endonucleases and homodimers that may be used in a nicking reaction involving strand displacement for fragmenting genomic DNA.

The nicking endonuclease used in the embodiments should be modification-sensitive in that it does not nick DNA if its recognition site contains a modified base. For example, Nt.CvipII (which is one of the many nicking endonucleases that could be used in the method) is a methylation sensitive nicking endonuclease that recognizes and cuts at the sequences CCD, where D=A, G or T (see, e.g., Chan et al., Nucleic Acids Research, 2004 32: 6187-6199). This sequence is found quite frequently in many genomes. In this example, the dNTP mix can contain 5-methyl-dCTP, and the fragments that are produced by the method may contain $^{5m}$C. Nt.CvipII does not nick at recognition sites that contain $^{5m}$C, and so the fragments are protected from further digestion by this enzyme.

The term "modification-sensitive nicking endonuclease" refers to a site-specific nicking endonuclease that nicks a double stranded DNA if the recognition sequence is composed of any or all of guanine, adenosine, thymine and cytosine bases but does not nick if a particular base in its recognition sequence (typically a cytosine) is modified.

There are many nicking endonucleases now available commercially (see for example the New England Biolabs catalog). Furthermore, it is straightforward to convert a heterodimeric restriction endonuclease into a nicking endonuclease by inactivating one of the two subunits. This has been described U.S. Pat. No. 7,081,358. Other methods of creating nicking endonucleases from restriction endonucleases have also been described (see for example U.S. Pat. No. 7,943,303, US 2005/0136462; and US 2008/0268507). Preferably a restriction endonuclease that has a suitable recognition sequence preferably a 3 base or 4 base recognition sequence may be selected that also has a sensitivity to modified bases such that it is blocked from nicking if a modified nucleotide is inserted into the recognition sequence. A sample of restriction endonucleases that are blocked by a methylated C are provided in the New England Biolabs 2015/16 catalog pg. 282-287 with recognition sequences provided on pg. 297-312. Some nicking endonucleases occur naturally such as BstNBI which is a dimer which becomes a monomer on purification because of the weak association of the two subunits. Other restriction endonucleases are monomers that recognize and nick one strand and then move to the second strand to form a nick there too (see for example UbaLAI (Sasnauskas, et al, Nucleic Acid Research (2017) 45, 9583-9594)). Because these enzymes nick sequentially, the one or more nick translating enzymes can initiate nick translation with modified nucleotides on one strand thereby blocking the monomer from nicking the second strand.

Generally, a nicking endonuclease retains the cleavage specificity of the restriction endonuclease from which it was derived. For purposes of present embodiments, it is desirable to select an enzyme that has a 3 base or 4 base recognition sequence on DNA, preferably a 3 base recognition sequence such as CviPII (Nt.CviPII that cleaves DNA after the third base in the recognition sequence i.e., 5' CCD/) or 4 base recognition sequence HNH (gHNH nicking endonuclease cleaves DNA at 5'CG/GT in the presence of magnesium ions or NN/NT in the presence of $Mn^{+2}$ ions). An advantage of Nt.CviPII is the frequency at which the CCD recognition sequence occurs within the genome, thereby permitting any DNA in the vicinity of a target protein to be nicked and labeled either for separation for sequencing or visualization by microscopy. Over 200 nicking endonucleases have been described. Many of these have been engineered from restriction endonucleases by inhibiting the cleavage activity on one strand of the DNA. This may be achieved for example, by mutating a subunit in a heterodimeric restriction endonuclease. Examples of nicking endonucleases are provided in U.S. Pat. Nos. 7,081,358 and 6,191,267.

Any nicking endonuclease may be used in NEFP. Specific examples include the following with recognition sequences provided in parenthesis after each nicking endonuclease where Nb is bottom strand nicking and Nt is top strand nicking: Nb.Bpu10I (CCTNAGC) Nt.Bpu10I (CCTNAGC) Nb.Mva1269I (GAATGC) Nt.Bst9I (GAGTC) Nt.AlwI (GGATC) Nb.BbvCI (CCTCAGC), Nt.BbvCI (CCTCAGC) Nb.BsmI (GAATGC) Nt.BsmAI (GTCTC) Nt.BspQI (GCTCTTC) Nb.BsrDI (GCAATG) Nb.BssSI (CACGAG) Nt.BstNBI (GAGTC) Nb.BtsI. (GCAGTG) Nt.CviPII (CCD) BsoBI (CYCGRG), gHNH (CG/GT) (see for example REBASE® (New England Biolabs, Ipswich, Mass.)).

Although the term "nicking endonuclease" is included in the acronym for NEAT-Seq, any type of specific nicking that can be blocked by specific modified nucleotides may be used to achieve embodiments of the method. For example, various Cas or argonaut proteins also sometimes referred to as restriction endonucleases, can be modified so as to nick rather than cleave DNA. Specificity for these enzymes comes from the associated specific guide nucleic acid.

Target Binding Moiety

Although in certain circumstances, it may be preferably to rely on an antibody that directly binds to a chromosomal target, alternatives are also possible. These include the use of antibodies that have a specificity for a molecule (for example a small molecule), that binds to the DNA binding protein. In FIG. 12A-12E, an antibody is shown that binds to SAH that in turn binds to DNMT-1. In certain embodiments, the nicking enzyme may be directly fused to a chromatin structure such as a G-quadruplex or R-loop, damaged nucleotide, crosslinked or modified nucleotide.

The term "antibody" refers to intact antibodies such as any of IgG, IgA, IgM, IgD, IgE and camelid antibodies and other isoforms. The term "antibody" also includes antibody fragments that have binding specificity to a target (sufficient Fab to enable binding) and as needed a portion of Fc for binding a protein such as Protein A, Protein G or Protein L. Although the various forms vary in their specificity and the ease in making antibodies recombinantly, modification of the protein structures and/or saccharides can provide appropriate binding kinetics for the present assay. The term "antibody" also refers to any of polyclonal or monoclonal antibodies.

Target binding moieties need not be antibodies. For example, target binding moieties may be antagonists or agonists of the target. These may be relatively small organic compounds or may be relatively large macromolecules such as biological molecules.

The "target" may be a protein that binds to DNA. Alternatively, the target may be a modified base such as methyl cytosine, hydroxymethyl cytosine, formyl cytosine or carboxy cytosine. These modifications of nucleotides in DNA are examples of modifications that have been recognized to be involved in transcriptional regulation in mammalian cells. Other nucleotide modifications are being revealed through work done on prokaryotic and viral DNAs. Any of these can be targets. The target also refers to a structural feature of a region of DNA such as a G-quadruplex that are associated with promoter regions in the genome and R-loops.

The "target" may also refer to damaged DNA or cross linked DNA.

Any of the above mentioned targets can be recognized by antibodies or other target binding moiety in NEAT-Seq and NEAT-View.

As shown in FIG. 11A-11G, a signal from a target may be amplified by the use of a secondary antibody that can bind on either of the two arms of the primary antibody.

Nicking Endonuclease-Fusion Protein.

According to an embodiment of the method, linking a nicking endonuclease of interest to a target on DNA may be achieved indirectly. By indirectly, it is meant that there is no chemical bound between the enzyme and the chromatin bound target (e.g., protein) of interest. The linkage occurs via a binding domain on the NEFP that recognizes a constant region in the antibody that in turn is bound directly or indirectly via another antibody to the target. Rabbit (alternatively mouse, or other) antibodies that have specificity for the target can be bound to the DNA binding protein in the chromatin region of the genome. Protein A, Protein G and Protein L are examples of an antibody binding moieties or domains that have an affinity for the constant region of IgG antibodies. These proteins have been fused to the nicking endonuclease without disrupting its cleavage activity as illustrated in FIG. 1A-1C. For example, it was found here that all or part of the staphylococcal Protein A or to all or part of Staphylococcal Protein G can be fused to a nicking endonuclease without interfering with the specificity or cleavage activity of the endonuclease (see for example, FIGS. 1B and 1C). In the examples below, the Protein A moiety contains the IgG binding domains of Staphylococcal Protein A. The NEFPs described in the examples are Protein A-gHNH, Protein G-gHNH, Nt.CviPII-Protein A. However, other proteins that have an affinity for the constant region of an antibody may also be used such as lectins. The antibodies or the NEFP or the dNTPs used in polymerase dependent DNA replication may advantageously be tagged, for example fluorescently tagged, which allows their detection and their localization. The antibodies and/or NEFP and/or dNTPs used in polymerase dependent DNA replication may also be tagged by biotin. The NEFP that has become associated with a target (e.g., protein) via an antibody or other binding moiety is referred to herein as "tethered" whereas an NEFP that is not bound to a target either directly or indirectly is referred to as "untethered".

In another embodiment, the nicking endonuclease may be fused to a binding moiety that binds directly to the target (see FIG. 12A-12E) and does not rely on an intermediate binding molecule such as Protein A.

Chromosomal Target

The chromosomal target for NEAT-Seq and NEAT-View maybe any of a DNA binding protein, a stable tertiary DNA structure such as a G-quadruplex, a modified nucleotide such as a methylated or hydroxymentylated cytosine and/or a damaged DNA such as a thymidine dimer or 8-oxoguanidine or cross linked nucleotides (see for example, FIG. 12A-12E).

The chromosomal target may be a DNA binding protein also referred to herein as a "target protein."

A target protein as used herein refers to a protein that binds specific sites in the chromatin region of the genome of a cell. Changes in the type of behavior of DBP can be used as markers for cancer and other pathologies so that their accurate mapping is of value in determining disease and the subsequent treatment of the patient. Normal or abnormal DBPs may be regulating genome expression, chromosomal replication or cellular proliferation function. Examples of DBPs include transcriptional activators and repressors. Other DBPs are associated with centromeres or with telomeres where their role comprises regulation of chromosome replication and maintenance.

Examples of DBP include Nucleophosmin (NPM1) also known as nucleolar phosphoprotein B23 or numatrin, is a protein that in humans is encoded by the NPM1 gene. The NPM1 gene is up-regulated, mutated, and chromosomally translocated in many tumor types. Chromosomal aberrations involving NPM1 were found in patients with non-Hodgkin lymphoma, acute promyelocytic leukemia, myelodysplastic syndrome, and acute myelogenous leukemia; and Lamin B2, a protein that in humans is encoded by the LMNB2 gene. It is the second of two type B nuclear lamins, and it is associated with laminopathies.

Non-sequence specific DBDs or DBDs that depend on another protein binding domain can also be interrogated. Such an example of a non-sequence specific DBD is the non-histone protein HP1 that has dosage dependent effects on heterochromatin mediated gene silencing. The N-terminal half of HPI is a chromodomain that shares high sequence similarity with another protein that is a silencer of homeotic genes and binds to distinct chromosomal sites. The chromodomain of HP1 proteins binds to methylated H3K9 and is required for its transcriptional repressive activity. Another related chromodomain of note is associated with SUV39H1.

Reduction of Background Noise by Preventing Binding of Untethered NEFP to Specific Recognition Sequences in DNA and/or Non-Specifical Binding to DNA A feature of embodiments of present methods and compositions is the ability to detect protein binding events in chromatin by increasing the signal to noise ratio. A source of background might arise from the non-specific binding of the NEFP directly to DNA rather than to antibodies bound to target. This problem has been solved by the addition of a heparin salt with the NEFP in a low salt buffer. Once the nicking endonuclease-fusion is bound to the antibody-target, the heparin salt can be washed away. Excess unbound and non-specifically bound NEFP are also removed with the heparin salt. In the workflow shown in FIG. 3A-3B, the heparin salt is added in a low salt buffer to cells followed by the addition of the NEFP preferably already in a low salt buffer. The low salt buffer is then replaced by a high salt buffer wash prior to the nick translation reaction to remove the heparin salt and excess NEFP that has not bound exclusively to the antibody bound target DNA binding protein. Protein A, Protein G and Protein L bind to antibodies with strong affinity (e.g., Kd=$10^{e7-13}$) and hence remain bound under conditions of a high salt wash.

The ability to reduce background noise and the choice of labeled nucleotides in the nick translation mixture, enable both analysis of binding of targets with visualization of the morphology of cells and the distribution of the targets within the cells using fluorescent dyes and DNA sequencing of DNA fragments resulting from nicking.

In present embodiments, heparin salt is provided in excess relative to the NEFP. For example, the NEFP may be provided to a sample at a concentration in the range of 100 ng to 1 µg whereas the heparin may be 1 mg in the same volume. The higher the concentration of NEFP added to a cell sample, the faster the reaction time. This is only possible because of the inhibition of nicking activity of unbound NEFP.

Inhibition of Nicking Endonuclease Activity of Untethered NEFPs

Masking DNA with a non-specific binding protein or reversibly blocking the activity of the nicking endonucleases by agonist Inhibition of nicking endonuclease activity is desirable until after excess untethered NEFP molecules have been removed from the sample by washing in the high salt buffer. The nicking activity of the NEFP molecules is initiated when metal ions such as magnesium salts or manganese salts are added to the sample. Removal of untethered NEFP molecules is preferably achieved prior to the addition of Mg or Mn ions to the sample.

"Inhibition" of an endonuclease refers to an activity that is too low to be detected, or is less than 10%, preferably less than 4% or less than 1% of the maximal rate of nicking under non-inhibitory conditions.

Nicking Activity

Once bound to the target to which a primary antibody has been attached, the activated NEFP can nick DNA in the 3D space around the tethered enzyme in a buffer that contains magnesium ions or manganese ions. However, nicking can be blocked if the recognition sequence contains a modified nucleotide. This modified nucleotide can be inserted during the first round of nick translation but is not present initially since native chromatin that is available for nick-translation rarely contains modified nucleotides at the nicking regions. Blocking a second round of nicking of the duplex after nick translation is a design feature of embodiments of the method that enhances the clarity of the resulting signal during mapping. This also prevents repeated nicking and loss of DNA.

Nick Translation

Nick translation has been generally performed using low concentrations of DNase, and DNA polymerase I enzymes where the DNase is used under conditions where the enzyme non-specifically nicks one strand in the DNA duplex. Nick translation was originally described for incorporating radiolabeled nucleotides into DNA (Rigby, et al. 1977, Journal of Molecular Biology vol 113, 237-251). Examples of strand displacing polymerases for use in nick translation may include the prokaryotic polymerase DNA Pol I and variants thereof such as Klenow Fragment (3'→5' exo, Bst DNA Polymerase, Large Fragment, Bst 2.0 DNA Polymerase (New England Biolabs, Ipswich, Mass.), Bst 3.0 DNA Polymerase (New England Biolabs, Ipswich, Mass.), Bsu DNA Polymerase, Large Fragment, phi29 DNA Polymerase (New England Biolabs, Ipswich, Mass.), Therminator™ DNA Polymerase (New England Biolabs, Ipswich, Mass.), certain archaeal polymerases, BSM DNA Polymerase, EquiPhi29™ DNA Polymerase (Thermo Fisher Scientific, Waltham, Mass.), and Manta 1.0 DNA Polymerase (exo–).

The polymerase repaired nick translated strand could become a substrate for additional nicking unless an inhibitory moiety, for example, a modified nucleotide, for example, a methylated cytosine, is incorporated into the nick translated DNA. In preferred embodiments, once nick translation has occurred, the nicking enzyme becomes blocked from nicking the DNA a second time.

Modified Nucleotides for Inhibiting Secondary Nicking Endonuclease Cleavage

Modified nucleotides and modified dNTPs include chemical groups that are covalently linked to the base or to the sugar. Modified bases include methylated purines or pyrimidines, acetylated purines or pyrimidines, alkylated riboses or other heterocycles, hapten or fluorescent labels. Modifications on the sugar moiety which may be ribose or deoxyribose include replacement of one or more of the hydroxyl groups with halogen atoms or aliphatic groups, or are functionalized as ethers, amines, or the like.

The term "dNTP mix" includes the four standard dNTPs—dGTP, dATP, dTTP and dCTP or one or more dNTPs can be partially or completely substituted by one or more modified dNTP. The dNTP mix enables a polymerase to extend by nick translation, a single strand DNA at a nick site, where the newly synthesized nucleic acid contains a mixture of standard nucleotides and modified nucleotides such that the nicking endonuclease can no longer nick the DNA in the newly synthesized DNA. In one example, the dNTP mix contains any one or combination of a modified dGTP, a modified dATP, a modified dTTP, and a modified dCTP along with a complement of standard dNTPs. In one embodiment, a modified dATP or a modified dCTP, or a combination of a modified dATP and a modified dCTP may be used. In some embodiments, the one or more modified dNTPs may replace some or all the corresponding unmodified dNTPs. Preferably dNTPs and modified dNTPs have a 3' hydroxyl so that after they are added to the chain by the polymerase, the polymerase can continue to extend the chain.

Base modifications to which modification sensitive nicking endonucleases are sensitive include nucleoside triphosphates that contain methylated purines or pyrimidines, acetylated purines or pyrimidines, alkylated riboses or other heterocycles such as 5mC, 5hmC, 5fC, 5caC, 5-bromocytosine, 5-propynylcytosine, 5-iodocytosine, 5-aminoallylcytosine, or 5-propargylaminocytosine, N6-methyladenine, N4-methylcytosine, 8-Oxo-2'-deoxyadenosine (8-oxo-dA), 8-Oxo-2'-deoxyguanosine (8-oxo-dG), O6-methylguanine (O6-m-dG), 1-methyladenine (1-m-dA), O4-methylthymine (O4-m-dT) and β-D-glucosyl-hydroxymethyluracil (Base J) as well as 6 modified adenosine (e.g., N6-methyladenosine and analogs thereof).

In any embodiment, the modified base may contain an affinity tag (e.g., an azide/alkyne group, which is suitable for conjugation to another moiety, e.g., a solid support via click chemistry, or a biotin group so that the labeled nucleic acid can be enriched on a suitable support) or an optically-detectable label (e.g., a fluorophore). The dNTP mix used in embodiments may vary. For example, the dNTP mix used may comprise any one or combination of a modified dGTP, a modified dATP, a modified dTTP, and a modified dCTP.

In one embodiment, a mixture containing dATP, dTTP, dGTP, and $d^{5m}$CTP is included in a reaction mixture for nick translation in addition to a strand displacing polymerase for blocking secondary nicking. Methylated cytosine may be selected as the preferred modified nucleotide for GC rich regions having many nicking enzyme sites adjacent to the target.

Other modified nucleotides may also be incorporated during nick translation to act as inhibitory moieties for nicking endonuclease cleavage. Examples include: Biotin-14-dATP, Biotin-14-dCTP, Bio-16-UTP, Biotin-14-CTP, Biotin-11-UTP, Biotin-11-UTP, 3'-Biotin-GTP, 3'-Desthiobiotin-GTP, Biotin-7-dATP, Biotin-11-dATP, Desthiobiotin-7-dATP, N6-(6-Aminohexyl)-3'-dATP-Biotin, EDA-ADP-Biotin, EDA-ATP-Biotin, 8-(6-Aminohexyl)-amino-ATP-Biotin, N6-(6-Aminohexyl)-ATP-Biotin, γ-(6-Aminohexyl)-ATP-Biotin, EDA-AppNHp (EDA-AMPPNP)-Biotin, (6-Aminohexyl)-amino-adenosine-2',5'-bisphosphate-Biotin, (6-Aminohexyl)-amino-adenosine-3',5'-bisphosphate-Biotin, γ-PEG8-ATP-Biotin NU-926-BIOγ-[(6-Aminohexyl)-imido]-ATP-Biotin, γ-[(PEG3-Amino)-imido]-ATP-Biotin, γ-[Ethyl-CONH-(PEG4)]-ATP-Biotin, Biotin-11-ddATP, 5'-Biotin-ApG NU-888-BIOBiotin-AMP, ATPγS-Biotin, Azido-ATP-γ-Biotin, ATP-acetyl-hex-Biotin Additionally, tagged nucleotides may be included in a reaction mixture, for example, biotinylated dCTP for incorporation into DNA during nick translation. Tags such as biotin may then bind to affinity reagent coated magnetic beads and the DNA purified for sequencing. These tagged nucleotides enable capture of nick translated DNA on an affinity binding substrate such as a streptavidin bead. In this way, the tagged nucleotides provide a means to enrich for the DNA fragments that contain the target. Although the size of the DNA fragments obtained following endonuclease cleavage and nick translation may vary, the range commonly observed is 200-600 bases, more particularly 250-400 bases, more particularly 300-350 base fragments.

Optionally, the DNA fragments of interest can be released from genomic DNA by subsequent reactions with free or bound nicking or restriction endonucleases that cleave the genome in regions where nick translation had not previously resulted in incorporation of blocking modified nucleotides.

Labeled dNTPs

One or several types of modified dNTPs may be used in the nick translation reaction. These may include one or more of an inhibitor of nicking endonuclease cleavage such as $d^{5m}$CTP DNA, a tagged nucleotide such as for example biotinylated dCTP and a nucleotide labeled with a detectable label such as a fluorescent or colored dye for in situ detection of the target. The modified nucleotides may be in addition to standard dNTPs (dCTP, dATP, dGTP and dTTP) or may substitute for one of these nucleotides. If more than one type of modified nucleotide is used, it may be the same or a different dNTP.

Alternatively, or in addition, fluorophore labeled dNTPs may also be used to enable visualization of the target within the cells by microscopy. Examples include Fluorescein-12-ddCTP, Fluorescein-12-ddUTP, Fluorescein-12-ddATP, ROX-ddUTP, ROX-ddATP, R6G-ddCTP R6G-ddATP. TAMRA-ddUTP, TAMRA-ddCTP, TAMRA-ddATP, TAMRA-ddGTP, Cyanine 3-ddATP Cyanine 3-ddGTP, Cyanine 5-ddCTP, Cyanine 5-ddUTP, Cyanine 5-ddGTP, R110-ddUTP, R110-ddCTP, R110-ddGTP, Fluorescein-12-dUTP, Texas Red®-5-dUTP, Lissamine-5-dUTP, Diethylamino-coumarin-5-dUTP, Cyanine 3-dUTP, Cyanine 5-dUTP, Fluorescein-12-dCTP, Texas Red®-5-dCTP, Cyanine 3-dCTP, Cyanine 5-dCTP, Fluorescein-12-dATP, Texas Red®-5-dATP, Cyanine 3-dATP, Cyanine 5-dATP, Fluorescein-12-dGTP, Cyanine 3-dGTP, Cyanine 5-dGTP, Fluorescein-12-UTP, Cyanine 3-UTP, Cyanine 5-UTP, Fluorescein-12-CTP, Cyanine 3-CTP, Cyanine 5-CTP, Fluorescein-12-ATP, AMCA-6-dUTP, DEAC-dUTP, dUTP-ATTO-425, dUTP-XX-AF488, dUTP-XX-AF488, dUTP-XX-ATTO-488, Rhodamine-12-dUTP, dUTP-XX-ATTO-532, dUTP-Cy3, dUTP-XX-Cy3, dUTP-XX-AF555, dUTP-ATTO-550, dUTP-Texas Red, dUTP-XX-Texas Red, dUTP-XX-AF594, dUTP-XX-594, dUTP-Cy5, dUTP-XX-Cy5, dUTP-ATTO-647N, dUTP-ATTO-643, dUTP-XX-ATTO-643, dUTP-XX-AF647, dUTP-ATTO-655, Rhodamine-12-dCTP, dCTP-Cy3, dCTP-ATTO-550, dCTP-Texas Red, dCTP-Cy5, dCTP-ATTO-647N, Aminoallyl-dUTP-Atto 425, Aminoallyl-XX-dUTP-Atto 488, Aminoallyl-XX-dUTP-Atto 532, Aminoallyl-dUTP-Atto 550, Aminoallyl-dUTP-Atto 647N, Aminoallyl-dUTP-Texas Red®, Aminoallyl-dUTP-Cy®3, Aminoallyl-dUTP-Cy®5, Propargylamino-dCTP-Cy®3, Propargylamino-dCTP-Cy®5, Mant-ADP, Mant-ATP, Mant-dATP, Mant-GDP, Mant-GTP, Mant-dGTP and TNP-GTP.

Applications

In embodiments of the method, NEFPs and antibodies may be introduced into living cells or fixed cells in a whole and intact state or as purified nuclei. This can be achieved by permeation of the cytoplasmic and nuclear membranes using for example Proteinase K that cleaves protein in the membranes or fixation with formalin.

In general, the steps of the method may be performed in a single reaction tube amenable to workflow automation. The method may be completed rapidly within 60 minutes. The method may be completed with relatively few cells from a sample for example, less than 1000 cells, for example less than 100 cells more particularly less than 50 cells, for example 25 cells or less.

Embodiments of this method may include an automated process that can receive a patient sample in a doctor's office or operating theater and can provide in real time, a sequence result defining the presence and genome location of targets that are indicators of pathology such as cancer. At the same time, the results can advise the clinician of suitable treatment in view of the presence or absence of targets. Moreover, by labelling nucleotides used in nick translation or by labelling the fusion nicking endonuclease with a detectable label such as a visible or fluorescent label in addition to biotinylated-dCTP and 5mCTP, the sample cells may be analyzed for overall morphological changes by microscopy. The assay time from addition of the antibody reagents to the fixed or unfixed biopsy sample followed by the NEFP to obtain fragments of DNA to obtain isolated biotin labeled DNA product may be achieved within a day or less.

In certain circumstances it may be desirable to perform histological analysis of a target prior to sequencing. Accordingly, the methodology follows steps described above.

The results show that DNA visualization around the target is substantially the same as direct staining of the target protein. Methods described here are a novel epigenomic technology combining cell biology and genomics for DBP/molecules. Without visualization, in situ DNA protein mapping technology can be performed.

NEAT-Seq Laser Microdissection (LCM) Histology and Genomics from One Sample

Samples of tissue can be obtained from a patient in an operating room or surgery or frozen or fixed cell samples (e.g., FFPE) can be retrieved from storage for histology and genomic analysis of target DBP, and their physical location in the cell nuclei and their specific genomic locations determined. The cell samples may be attached to glass cover slips or slides with the aid of gelatin or other suitable matrix to aid their adherence to the solid substrate. The cells are fixed using routine methods involving methanol, ethanol, formaldehyde or other agent that cross links proteins. In addition, the cells are treated with an agent such as Triton X that causes the cytoplasmic and nuclear membrane to become permeable (see for example Thermo Fisher Scientific, Waltham, Mass.). Again, using routine immunocytochemistry techniques (Estève, et al. (2006) Genes & Development 20: 3089-3103) primary antibodies are added to the immobilized permeabilized cells or permeabilized cells in solution where the antibodies bind the target. Optionally blocking agents such as BSA can be added with the primary antibody but is not a requirement of embodiments herein. A secondary antibody may also be added but again this is optional. The secondary antibodies bind to the primary antibody and amplify the signal in standard protocols described for detecting fluorescence in a histology sample. In embodiments described herein, the secondary antibody may contribute to reducing the signal to noise ratio but since the present embodiments have very little background noise in the first place, the use of a secondary antibody is considered optional.

Features that make NEAT-Seq special when compared to existing methods include one or more of the following:

(1) In NEAT-Seq, DNA associated with a target is immobilized on beads and remaining chromosomal material is washed away. In contrast, other methods trap the unwanted material and release the target DNA in eluate;

(2) In NEAT-Seq, there is inhibition and removal of non-specific binding to naked DNA whereas no inhibition of non-specific binding of fusion protein to naked DNA occur in other methods;

(3) The sensitivity of NEAT-Seq is greater than compared to other methods. There is greater signal to noise ratio. This is in part because of prevention of non-specific binding of fusion proteins to non-target DNA that enables higher concentrations of NEFP for targeting rare targets in chromosomal DNA in a relatively shorter incubation period than would otherwise be possible;

(4) NEAT-Seq is effective on fixed and unfixed cells;

(5) NEAT-View can provide visualization of histology samples followed by sequencing of the same samples because of the use of dyes along with biotin labeled methylated cytosine in the nick translation assay. This is not possible with other methods;

(6) NEAT-Seq can provide sequence data using less than 50 cells in starting material which is orders of magnitude less than other methods. Degradation of target DNA is avoided because a sequence specific nicking endonuclease is used and modified nucleotides block nicking endonuclease activity so that less starting material is required. No equivalent inhibition occurs with other enzyme cleavage methods;

(7) In NEAT-Seq, there are less manipulation steps where for example, DNA purification steps are not required. The entire sample preparation up to library preparation can be performed in one tube in a day or less. This is more rapid than other techniques; and (8) Using NEAT-Seq/View, the same tissue sample can be analyzed for histology under a microscope and by DNA sequencing.

General Considerations

Unless otherwise defined, all technical and scientific terms used herein have the same meaning as commonly understood by one of ordinary skill in the art to which this disclosure belongs. Still, certain terms are defined herein with respect to embodiments of the disclosure and for the sake of clarity and ease of reference.

Sources of commonly understood terms and symbols may include: standard treatises and texts such as Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); Singleton, et al., Dictionary of Microbiology and Molecular biology, 2d ed., John Wiley and Sons, New York (1994), and Hale & Markham, the Harper Collins Dictionary of Biology, Harper Perennial, N.Y. (1991) and the like.

As used herein and in the appended claims, the singular forms "a", "an", and "the" include plural referents unless the context clearly dictates otherwise. For example, the term "a protein" refers to one or more proteins, i.e., a single protein and multiple proteins. The claims can be drafted to exclude any optional element when exclusive terminology is used such as "solely," "only" are used in connection with the recitation of claim elements or when a negative limitation is specified.

Aspects of the present disclosure can be further understood in light of the embodiments, section headings, figures, descriptions and examples, none of which should be construed as limiting the entire scope of the present disclosure in any way. Accordingly, the claims set forth below should be construed in view of the full breadth and spirit of the disclosure.

Each of the individual embodiments described and illustrated herein has discrete components and features which may be readily separated from or combined with the features of any of the other several embodiments without departing from the scope or spirit of the present teachings. Any recited method can be carried out in the order of events recited or in any other order which is logically possible.

Numeric ranges are inclusive of the numbers defining the range. All numbers should be understood to encompass the midpoint of the integer above and below the integer i.e., the number 2 encompasses 1.5-2.5. The number 2.5 encompasses 2.45-2.55 etc. When sample numerical values are provided, each alone may represent an intermediate value in a range of values and together may represent the extremes of a range unless specified.

In the context of the present disclosure, "non-naturally occurring" refers to a polynucleotide, polypeptide, carbohydrate, lipid, or composition that does not exist in nature. Such a polynucleotide, polypeptide, carbohydrate, lipid, or composition may differ from naturally occurring polynucleotides polypeptides, carbohydrates, lipids, or compositions in one or more respects. For example, a polymer (e.g., a polynucleotide, polypeptide, or carbohydrate) may differ in the kind and arrangement of the component building blocks (e.g., nucleotide sequence, amino acid sequence, or sugar molecules). A polymer may differ from a naturally occurring polymer with respect to the molecule(s) to which it is linked. For example, a "non-naturally occurring" protein may differ from naturally occurring proteins in its secondary, tertiary, or quaternary structure, by having a chemical bond (e.g., a covalent bond including a peptide bond, a phosphate bond, a disulfide bond, an ester bond, and ether bond, and others) to a polypeptide (e.g., a fusion protein), a lipid, a carbohydrate, or any other molecule. Similarly, a "non-naturally occurring" polynucleotide or nucleic acid may contain one or more other modifications (e.g., an added label or other moiety) to the 5'-end, the 3' end, and/or between the 5'- and 3'-ends (e.g., methylation) of the nucleic acid. A "non-naturally occurring" composition may differ from naturally occurring compositions in one or more of the following respects: (a) having components that are not combined in nature, (b) having components in concentrations not found in nature, (c) omitting one or components otherwise found in naturally occurring compositions, (d) having a form not found in nature, e.g., dried, freeze dried, crystalline, aqueous, and (e) having one or more additional components beyond those found in nature (e.g., buffering agents, a detergent, a dye, a solvent or a preservative). All publications, patents, and patent applications mentioned in this specification including U.S. Provisional 63/038,469, filed Jun. 12, 2020, are herein incorporated by reference to the same extent as if each individual publication, patent, or patent application was specifically and individually indicated to be incorporated by reference.

EXAMPLES

Any reagents, unless otherwise specified, may be obtained from New England Biolabs, Ipswich Mass.

Example 1: Construction, Purification, and Activity Assay for NEFP (pA/G-Nt.CviPII and pA/G-gHNH)

A. Protein G-gHNH and Protein A-gHNH Fusions

Protein G-gHNH and Protein A-gHNH bifunctional fusion proteins were constructed by creating synthetic genes encoding the DNA nicking domain of phage gamma HNH nicking enzyme (phi-gHNH), an amino acid sequence linker (GSATGTSAGSTG (SEQ ID NO:2) and IgG or a linker GSATIV (SEQ ID NO:1) and IgA binding domains (see FIG. 1A). Abbreviations: Protein A is referred to in the Figures as pA, Protein G as pG, Protein L as pL. pG+L refers to a tandem linkage of Protein G and Protein L. pG/L refers to protein G or protein L, pG/A refer to Protein G or Protein A.

The synthetic genes were cloned into pTXB1 (New England Biolabs, Ipswich, Mass.) and assembled with NEBuilder® HiFi DNA Assembly Master Mix (New England Biolabs, Ipswich, Mass.). The plasmids with the inserts were sequenced to verify the correct sequence. The fusion enzymes were purified using affinity chromatography on a chitin column. The enzymes were further purified from potentially contaminating nucleic acids by binding to DEAE resin in 0.3 M NaCl (i.e., nucleic acids bind to the resin at high salt and protein remains in the solution).

Protein G/A-gHNH fusion nicking activity was tested on pBR322 circular double stranded DNA using NEBuffer 2 in which magnesium ions were replaced by the same amount of manganese ions (1 mM). 1 µg of plasmid was used with 0.03 to 2 units of Protein G/A-gHNH fusion enzyme in a two-fold serial dilutions (2, 1, 0.5, 0.25, 0.125, 0.06, 0.03 units) in a total volume of 50 µl incubated at 37° C. for 1 hour. 10 µl of DNA loading dye mix (5×) was added to the nicked DNA. The nicked DNA samples were resolved on a 1% agarose gel and visualized under UV light. DNA fragment size was estimated along with 2 log DNA ladder (New England Biolabs, Ipswich, Mass.) and positive control Nt.CviPII (2 units) of the non-fused nicking endonuclease, (New England Biolabs, Ipswich, Mass.) digested pBR322 DNA (FIG. 1B). The fusion protein (Protein G-gHNH fusion) was observed to partially digest DNA at 0.03 units and completely digest the DNA at greater than 0.06 units. It was concluded from the assay that the nicking endonuclease-Protein G/A fusions had comparable nicking activity to the corresponding non-fused nicking endonuclease. A representative figure supporting this conclusion is provided in FIG. 1B for Protein G-gHNH fusions.

B. Nt.CviPII-Protein A Fusions

Nt.CviPII-Protein A fusions were constructed by creating synthetic genes that encoded Protein A at the C terminus of a C-terminal truncated Nt.CviPII via a linker GSGSGS (SEQ ID NO:3). The synthetic genes were cloned into an expression construct and purified as described above for gHNH and illustrated in FIG. 1A.

Nt.CviPII-Protein A fusion nicking activity was tested on pUC19 circular double stranded DNA in NEBuffer 2. The reaction conditions included 1 µg of pUC19 plasmid and 0.03 to 40 units of Nt.CviPII-Protein A fusion enzyme in a two-fold serial dilutions (40, 20, 10, 5, 2.5, 1.25, 0.06 and 0.03 units) in a total volume of 50 µl, was incubated at 37° C. for 1 hour. The fusion protein showed similar nicking activity to that of Protein G-gHNH where a concentration of greater than 0.06 units could substantially completely nick the DNA substrate forming small fragments. DNA fragment size was estimated along with 2 log DNA ladder and positive control Nt.CviPII digested pBR322 DNA. A unit definition was determined based on native Nt.CviPII where one unit of enzyme was able to digest 1 µg of plasmid DNA in a 50 µl reaction volume at 37° C. in one hour. It was concluded from the assay that the nicking endonuclease-Protein G/A fusions had comparable activity to the corresponding non-fused nicking endonuclease. A representative figure supporting this conclusion is provided in FIG. 1C for Nt.CviPII-Protein A fusions.

Example 2: Heparin Salts Compete with and Inhibit Binding NEFP to DNA and Thereby Indirectly Prevent Non-Specific Nicking A. Heparin Salts Inhibit Non-Specific DNA Binding and Nicking Activity of Untethered Nt.CviPII-Protein A Fusion To determine the effect of heparin sodium salt on the inhibition of nicking activities of Nt.CviPII-Protein A fusion, reaction tubes containing 10, 5, 2.5, 1.25, 0.62, 0.31, 0.15, and 0 mg/ml heparin, sodium salt were added to a 50 μl reaction, consisting of 5 μl 10×NEBuffer 2, 2.5 units Nt.CviPII-Protein A (as described in Example 1(B)), and 0.5 μg pUC19 DNA and incubated for 40 minutes 37° C. 10 μl of DNA loading dye mix (5×) was added to the samples and were resolved on a 10% polyacrylamide gel. The gel was stained with SYBR® Green (Molecular Probes, Eugene, Oreg.) and scanned on a Typhoon® imager (GE Healthcare Bio-Sciences, Marlborough, Mass.). Heparin sodium salt was shown to have a substantial inhibitory effect on nicking and subsequent cleavage of pUC19 DNA, with total inhibition occurring between 0.15-0.31 mg/ml heparin, sodium salt (FIG. 2A).

B. Inhibition of Nicking Activity is Due to Inhibition of Binding Between DNA Substrate and Fusion Enzyme Caused by Heparin To establish that the inhibitory effect of heparin, sodium salt in untethered Nt.CviPII-Protein A fusion activity was due to selective dissociation between DNA substrate and fusion enzyme, a gel-shift assay was performed. Double stranded DNA substrate containing constant amounts of Nt.CviPII binding domains (CCA, 5'GATCGTT-CACCAGTACACAGTAATTCG-F, F=fluorescein (SEQ ID NO:9)) and 3.2 μM Nt.CviPII-Protein A fusion were combined in the presence of 1×NEBuffer 2 in the absence of magnesium for 30 minutes at room temperature to enable an enzyme-substrate complex to be formed. Increasing amounts of heparin, sodium salt (0, 2.3, 4.6, 1, 20, 42, 83, 166, 330 μg/ml) was added to the total 50 μl reaction volume. It was observed that a heparin concentration of greater than 0.2 mgs/ml (at least 10 ng/μl or 10 mg/ml) enabled complete dissociation of the DNA-Nt.CviPII-Protein A complex as observed by the appearance of bands corresponding to DNA alone in a native 6% retardation gel (Thermo Fisher Scientific, Waltham, Mass.). It was concluded that Heparin causes dissociation Nt.CviPII-Protein A fusions from the bound substrate DNA (FIG. 2B).

C. Heparin Salt does not Interfere with the Formation of the Antibody-Protein A/G Complex To determine the effect of heparin on the formation of the antibody-Protein A/G complex, 5 mgs of immobilized and covalently cross-linked protein A/G magnetic beads were bound to 50 μgs of IgG molecules in a 50 μl reaction volume containing 1×PBST at room temperature for 30 minutes. The complex was washed 3 times using 1 ml of 1×PBST and incubated with 0.125, 0.25, 0.5 and 1 mg/ml Heparin for 30 minutes at room temperature in 25 μl total volume. The bead-bound (B) and unbound or bead elution (E) fractions were collected, SDS sample buffer (New England Biolabs, Ipswich, Mass.) was added and the samples were incubated at 95° C. for 5 minutes. Both B and E samples were resolved on tricine 10% acrylamide gel and stained for protein. Indeed, bead bound samples displayed both light and heavy chain of the antibody, confirming that Heparin cannot dissociate Protein A/G-antibody reaction (FIG. 2C).

In summary, heparin molecules only disrupt binding between nicking enzyme-Protein A/G fusion and DNA in the presence of a low salt buffer, but not between nicking enzyme-Protein A/G fusion and antibody (FIG. 2E, 2F). The beneficial effect of adding heparin salts during a NEAT-Seq or NEAT-View workflow is evidenced by significant reduction in background noise and enables the use of substantially fewer cells for sequencing in NEAT-Seq and more specific and informative visualization in NEAT-View than required in the absence of heparin salts.

Example 3: NEAT-Seq to Determine the Genome Sequence Location of Target in or on DNA The NEAT-Seq methodology used for visualization and subsequent sequencing of the DNA binding sequences of target protein in this example is described schematically in FIGS. 3A and 3B.

A. Determining the Location of Specific DNA Bound Proteins in Cell Cultures or Tissue Samples by Sequencing About 25,000 mammalian cells (HCT116) from a cell culture were cross-linked by treating with 1% formaldehyde for 10 minutes at room temperature followed by quenching of the cross linking reaction with 125 mM glycine. A cytosolic buffer (15 mM Tris-HCl pH 7.5, 5 mM MgCl2, 60 mM KCl, 0.5 mM DTT, 15 mM NaCl, 300 mM sucrose and 1% NP40) was added to the cross-linked cells to disrupt the cell membrane and cytoplasm enabling removal of the cytoplasmic fraction and the precipitation of nuclei. The nuclei pellet was resuspended in 1×PBST containing 1×PBS supplemented with 5% BSA (W/V) and 0.3% Triton™ X-1000 (V/V) (Millipore Sigma, Burlington, Mass.). The resuspended permeabilized nuclei were then treated as described below in preparation for sequence analysis.

B. Determining the Location of Specific DNA Bound Proteins from 5 uM Sections of FFPE Tissue Embedded in Paraffin by Sequencing The paraffin was removed by incubating the slides at 52° C. for 20 minutes with mineral oil (Millipore Sigma, Burlington, Mass.), followed by a series of 5 minute ethanol washes (100%, 90%, 80%, 70% and 0% v/v ethanol in water) at room temperature to rehydrate the samples. The slides were incubated in 1×PBST buffer (1×PBS in 0.1% Tween 20) first at 65° C. for 1 hour followed by 1×PBST with protease inhibitor (Millipore Sigma, Burlington, Mass.) at room temperature for 10 minutes followed by a 1×PBS wash to remove disrupted cell membrane and cytoplasm leaving permeabilized nuclei for further preparation for library making and sequence analysis. All reactions till DNA extraction could be performed on the slide or in solution.

C. Determining the Location of Specific DNA Bound Proteins in Nuclei by Visualization HCT116 cells cultured in six-well plates containing coverslips were grown overnight to 50-70% confluence on the coverslips in Dulbecco's Modified Eagle's Medium (DMEM) (GIBCO #12491, Thermo Fisher Scientific, Waltham, Mass.)+10% FBS+2 mM L-Glutamine. These cells were then cross-linked using 1% formaldehyde for 10 minutes at room temperature and quenched using 125 mM glycine. Cytosolic buffer described in (i) was added to cross linked cells and after a 10 minute incubation, the cell membranes and cytoplasm could be removed by washing with 1×PBS leaving behind permeabilized nuclei on the coverslips. Permeabilized fixed nuclei were blocked with 1×PBS supplemented with 5% BSA and 0.3% Triton™ X-100 for one hour at room temperature.

Binding of Antibody, and Labeling Reaction

Using the nuclei prepared by (i) or (ii) above, 2 μg of a single antibody selected from Pol II and H3K27ac (transcriptionally active) H3K27me3 (transcriptionally inactive), Pol II, phospho CTD and transcription factor YY1 was added to the nuclear pellet and incubated overnight at 4° C. in the presence of heparin sulphate (Millipore Sigma, Burlington, Mass.). Shorter incubation times may be used such as 10-30 minutes at a raised temperature such as 37° C. as described below. 1 μL of Protein A-gHNH (2 μ/μL) was added to the resuspended nuclei and after a 1 hour incubation at 4° C., the nuclei washed in 1×PBST supplemented with 500 mM NaCl to remove the heparin and excess Protein A-gHNH. 10 mM MnCl2 was added to a standard nick translation master mix containing DNA polymerase I, and a mixture of Biotin-d$^{5m}$CTP, dTTP, dGTP and dATP and the master mix was added to the nuclei to a final 1× concentration to activate bound gHNH cleavage of DNA. The reaction was incubated for 30 minutes at 37° C. and terminated with the addition of EDTA (0.5 M) and RNase with a further incubation for 1 hour at 37° C. Proteinase K and 20 μl of 20% SDS were added for an overnight incubation at 65° C.

Genomic DNA Isolation, NEAT-Seq Labeled DNA Capture, Next-Gen Library Preparation, Sequencing, and Sequence Analysis Genomic DNA was purified from the nuclei of 250,000 HCT116 cells (FIG. 4A and FIG. 4B) or from human liver FFPE sections (FIG. 4C) after the Proteinase K treatment step using a FFPE DNA purification kit (Qiagen, Hilden, Germany) yielding about 200 ngs DNA. The DNA was sonicated into 150 bp fragments (Covaris, Woburn, Mass.) and the entire reaction product was mixed with 20 μl of streptavidin coated magnetic beads (Invitrogen 65001 (Thermo Fisher Scientific, Waltham, Mass.)), blocked using 0.1% cold fish gelatin in 1×PBS overnight at 4° C. in B&W buffer (10 mM Tris-HCl pH 8.0, 1 mM EDTA, 2 M NaCl). Biotin-labeled open chromatin DNA fragments were captured by the streptavidin coated beads. Illumina adaptors were ligated onto the DNA (New England Biolabs, Ipswich, Mass., E7370S). 10-20 μl of bound DNA was used for library amplification using PCR (New England Biolabs, Ipswich, Mass., E7370S). Routinely 8-10 PCR cycles were used to generate enough amount of library DNA for sequencing. The number of cycles of amplification could be increased to for example, 12-13 cycles for samples derived from 100 fold fewer cells (250-500 cells) than the 25,000 cells used here. The library was examined and quantitated with high-sensitive DNA chip (Agilent, 5067-4627). The libraries were sequenced using an Illumina sequencing platform.

Data Analysis

Data processing and peak calling: Adaptor and low-quality sequences were trimmed from paired-end sequencing reads using Trim Galore with the following setting: --clip_R1 4 --clip_R2 4 --three_prime_clip_R1 4 --three_prime_clip_R2 4. Trimmed read pairs were mapped to the reference genome (mouse: mm10; human: hg38) using Bowtie2 Langmead et al. (2012) Nature Methods 9, 357-359 with the following arguments: --dovetail --no-unal --no-mixed --no-discordant --very-sensitive -I 0 -X 1000. Prior to peak calling PCR duplicates and mitochondrial reads were removed and only properly aligned read pairs were used for peak calling with MACS2 (9) using 'macs2 callpeak -f BAMPE -m 4 100 --bdg -SPMR'. Fraction of reads in peaks (FRiP): The FRiP score was calculated using the deepTools plotEnrichment function (Ramirez et al., 2016 Nucleic acid Research, 8, 44). Called peaks were classified into 2 groups: TSS peaks if they overlap with +/−500 bp from annotated TSSs (based NCBI RefGene annotation); and distal peaks if otherwise. Correspondingly, reads that overlapped with the TSS peaks by at least 1 base were marked as "TSS" reads. Reads that overlapped with distal peaks were marked as "distal" reads. Reads that do not overlap with any called peaks were marked as "reads not in peaks".

Peak overlap analysis: Peaks called from different experiments were compared using the Bedtools (Quinlan, et al, 2010 BioInformatics, 26, 841-842). First peaks from all the samples are concatenated. Peaks that have at least one base pair overlapping are considered associated and are merged to form a union peak set. Then peaks of individual samples were compared to the union set and were marked as either "unique" or "common". Last the numbers of "unique" and "common" peaks were summarized from all the samples and were used to make Venn Diagrams in R.

Correlation Analysis

Correlation analysis of UniNicE-seq open-chromatin signals were performed with the DiffBind (Ross-Innes et al., 2012 Nature, 481, 389-393) package in R and deepTools (Ramirez et al., 2016) using two methods: occupancy (peak overlap) based method uses peak overlapping states and affinity (normalized read density) based method. The occupancy-based method determines the correlation coefficients based on the numbers of unique peaks and overlapping peaks. The affinity-based method first determines the number of normalized reads that overlap with a set of consensus peaks for individual samples and then calculates Pearson correlation based on the normalized read count matrix. PCA plots were generated from the normalized read count matrix by the affinity method.

Peak annotation and Gene/Genome Ontology analysis: Functional annotation of called peaks was performed with HOMER (14) annotatePeaks.pl. After associating peaks with nearby genes and assigning peaks to different genomic features (e.g., promoter, exon, CpG islands, repetitive elements etc.), we also conducted Gene Ontology enrichment analysis for selected sets of UniNicE-seq peaks (e.g., tissue-specific peaks) and tested for enrichment of UniNicE-seq peaks in associated genomic features with HOMER.

External Datasets

TSS of mouse (mm 10) and human (hg38) genomes were extracted from the NCBI Ref Gene table downloaded from the UCSC Table Browser. The antibodies used here for NEAT-Seq reaction on cultured cells were for transcriptionally active gene histone marks, Pol II and H3K27ac, to enable comparison of the NEAT-Seq data with traditional chromatin immunoprecipitation (ChIP-seq). H3K27ac antibody incubated with cells for 10 or 30 minutes gave equal signal to noise ratio and was highly comparable with Pol II position on the genes. All NEAT-Seq data were comparable to ChIP-seq and control IgG antibody displayed no signals (FIG. 4A). However, the amounts of cells used for NEAT-Seq to obtain comparable results was 40 folds less than ChIP-seq (250K vs. 10000K).

When NEAT-Seq was used to compare transcriptionally active marks with inactive marks, the expected inverse correlation between active and inactive transcriptional marks was observed (FIG. 4B) confirming the utility of the NEAT-Seq method.

Human liver FFPE tissue sections also displayed H3K27ac enrichment at the transcription start site, provided median DNA fragment length was around 1 Kb (FIG. 4C). A comparison between NEAT-Seq and ChIP-seq for numbers of detected enriched H3K27ac region in HCT116 genome displayed significant conservation as displayed by overlapping peaks (FIG. 5).

Example 4: NEAT-View for Labelling, Visualizing and Quantifying Target DNA Bound Protein Permeabilized nuclei for visualization were prepared as described in Example 3(C). The HCT 116 nuclei on coverslips were probed with Nucleophosmin (FC-61991) Mouse Monoclonal Antibody (Thermo Fisher Scientific, Waltham, Mass. #32-5200), Lamin B2 Antibody (PA5-29121) (Thermo Fisher Scientific, Waltham, Mass. #PA5-29121) or HP1 alpha polyclonal antibody (Thermo Fisher Scientific, Waltham, Mass. #PA5-82556) at 2 µg/ml overnight at 4° C. Cells were washed with 1×PBS supplemented with 0.3% Triton X-100. The figures show the results obtained with Nucleophosmin (NPM1 nucleolar phosphoprotein B23) and HP1 alpha. In this example, a secondary antibody was used as described in FIG. 9. However, the secondary antibody is optional.

The permeabilized nuclei were treated with Goat anti-Mouse IgG (H+L) Superclonal™ Secondary Antibody, Alexa Fluor® 488 conjugate (Thermo Fisher Scientific, Waltham, Mass. #A28175) at a dilution of 1:2000 in 1×PBS, 0.3% Triton X-100, 0.1% BSA for 45 minutes at room temperature. Plates were then washed in 1×PBS, 0.3% Triton X-100 to remove unbound secondary antibody.

Nt.CviPII-Protein A was used for nicking specific DNA sequences adjacent to the DNA binding protein. In order to prevent Nt.CviPII-Protein A from preferentially binding non-specifically to nuclear DNA, cells were incubated for 10 minutes in 20 mM potassium phosphate pH 7.0, 1 mM EDTA, 20 mM NaCl$_2$, 0.3% Triton X-100, 0.1% BSA supplemented with 1 mg/ml Heparin Sodium Salt (Millipore Sigma, Burlington, Mass. #H3149). 2 units of Nt.CviPII-Protein A (~2000 U/ml) were diluted into 5 mls of the above buffer. After a 45 minute incubation at room temperature, the cells were washed with 20 mM potassium phosphate pH 7.0, 1 mM EDTA, 1M NaCl$_2$, and 0.3% Triton X-100. The high salt wash accomplished two functions: 1) it removed excess unbound Nt.CviPII-Protein A; and 2) it dissociated the heparin from the active site of the Nt.CviPII DNA binding/nicking moiety, rendering it competent to preform catalysis. For compact chromatin cells were incubated at 55° C. for 2-8 hours prior to NEAT-View/-Seq reaction to aid in labeling.

DNA that was within the range of the antibody-Protein A-nicking enzyme complex was labeled during nick translation by incubating the nuclei in 10 U of DNA polymerase I (New England Biolabs, Ipswich, Mass. #M0209S) and 30 µM of each dNTP (New England Biolabs, Ipswich, Mass. #N0447S) including 6 µM of Texas Red-5-dATP (PerkinElmer, Waltham, Mass. #NEL47100EA) and 1×NEBuffer 2 containing Mg ions in 800 µl total volume.

The labeling reaction was carried out at 37° C. for 1.5 hours in a humified incubator. Cover slips with bound nuclei were washed in the above high NaCl buffer, and then dried, mounted on slides, and stained with SlowFade® Gold Antifade Mountant with DAPI (Thermo Fisher Scientific, Waltham, Mass. #S36938). Labeled cell were visualized on a Zeiss confocal microscope (Zeiss, Dublin, Calif.).

As expected, antibody only based detection (FIG. 7A, FIG. 7B left panel) and NEAT-Seq based DNA labeling detection (FIG. 7A, FIG. 7B mid panel) overlapped (FIG. 7A, FIG. 7B right panel), demonstrating the utility of the technology.

Example 5: One-Tube NEAT-Seq without DNA Purification and Sonication

Cell preparation and labeling is described in Example 2. A detail flow diagram is shown in FIG. 8. In brief, 250K HCT116 cells (ATCC, Manassas, Va. #CCL-247) fixed using 1% formaldehyde. The cytoplasm was extracted by adding cytosolic buffer to the cells and keeping it on the ice for 20 minutes. Cells were collected by centrifugation at 3000 rpm for 10 minutes at 4° C. The supernatant was removed, and cellular pellet was used for antibody probing. The cells were suspended in 1 mL of PBST buffer supplemented with 0.1% BSA (Millipore Sigma, Burlington, Mass. #05470) and antibody, H3K27ac (Cell Signaling Technology, Danvers, Mass. #8173) and Incubate it for overnight at 4° C. in the presence of 1% heparin. 1 µL of Protein A/G-Nt.CviPII (2 µ/µL) was added into the reaction tube and incubated for 4 hours at room temperature to allow specific antibody-Protein A/G-Nt.CviPII complex formation. A magnetic rack was used to remove heparin magnetic beds to remove non-specific Protein A/G-HNH/Nt.CviPII. Rest of labeling components comprising of 20 µL of 10× buffer, 20 µL of 10 mM MnCl2, 1 µL of DNA polymerase I, 3 µL of Biotin-5mC-dNTP mixture (New England Biolabs, Ipswich, Mass. #N046S, Millipore Sigma, Burlington, Mass. #19524019, #19518018), 100 µL of 1×PBS (Thermo Fisher Scientific, Waltham, Mass. Gibco #70011-044), and 55 µL of MiliQ®-water (Millipore Sigma, Burlington, Mass.) was added. The labeling reaction was performed at 37° C. for 30 minutes at 37° C. Next, 20 µL of EDTA (Thermo Fisher Scientific, Waltham, Mass. Invitrogen #15575-038), and 2 µL of RNase (Thermo Fisher Scientific, Waltham, Mass. Invitrogen #12091021), was added and incubated for 1 hour at 37° C. 20 µL of Proteinase K and 20 µL of 20% SDS (Teknova, Hollister, Calif. #S0295) was added for to the tube and incubated overnight at 65° C. to digest protein and decrosslink. Proteinase K was heat inactivated by incubating the tube at 95° C. for 2 minutes. This step ensured genomic DNA free from crosslinked protein in the tube. In the next step, Nt.CviPII was added to the DNA overnight at 37° C. to digest non-$^{5m}$C containing DNA (note CpG methylated DNA of the mammalian genome will be destroyed by Nt.CviPII). Heat inactivation of Nt.CviPII was carried out by incubating the tube at 65° C. for 10 minutes. This DNA was directly used for NEAT-Seq library preparation on streptavidin magnetic beads, sequencing and sequence analysis as described in Example 3. The cell numbers could be lowered for library preparation to 5K.

Example 6: Visualization of DNA Binding Protein in Tissue Section, Laser Dissection Capture of Specific Region and NEAT-Seq Frozen tissue sections on slides were typically 5-10 µM thickness. The tissue sections were gently thawed by placing it at room temp for 2 minutes. The tissue section was fixed to the slide by treating with 1% formaldehyde or methanol for 10 minutes at room temperature and quenched by using 125 mM glycine. After 1×PBS wash, the slide was treated with cytosolic buffer (15 mM Tris-HCl pH 7.5, 5 mM MgCl2, 60 mM KCl, 0.5 mM DTT, 15 mM NaCl, 300 mM sucrose and 1% NP40) for 10 minutes at 4° C. The slide was washed with 1×PBS and incubated with primary antibody for overnight at 4° C. Unbound primary antibodies are washed away by 3 time rising of the slide with 1×PBS+0.3% Triton X (PBST). The tissue section was further incubated with secondary antibody for 45 minutes at room temperature. Unbound antibodies were washed away by washing 3 times with PBST. Tissue section was then washed 1× in 20 mM potassium phosphate buffer pH 7.0, 20 mM NaCl2 supplemented with 1 mg/ml Heparin. Tissue section was incubated with labeling reaction mix containing 1 µl (4 units) Nt. CviPII-Protein G or A in 1× in 20 mM potassium phosphate buffer pH 7.0, 20 mM NaCl2 supplemented with 1 mg/ml Heparin for 45 minutes at room temperature. Tissue section were further washed three times in PBST. 200 µl of the labeling buffer was placed on the tissue section and the slide was transferred to a humidified chamber at 37° C. for 2 hours (extension reaction contained Pol I 10 unit, Fluorescent or Biotin or both NTP's 1.5 hours 37° C.). The tissue section was washed 3 times in PBST. At this stage slides could be mounted for visualization. A detailed flow diagram is shown in FIG. 9.

Laser dissection capture of tissue samples will follow manufacturer's suggested protocol to isolate tissues from areas of interest. One-tube NEAT-Seq without DNA purification and sonication protocol (example 5), could be followed for Nextgen sequencing library making and data analysis. A detailed flow diagram is shown in FIG. 9.

Example 7: A Tripartite Protein A-DNA Polymerase I-Nicking Enzyme Fusion Anchors on Antibody and Facilitates NEAT-Seq on Nicked and Damaged DNA Samples Clinical samples, for example archival FFPE are highly nicked and damaged, thus are not suitable for nicking enzyme based NEAT-Seq. Since a free DNA polymerase would incorporate nucleotides at any nicked site including Nt.CviPII-Protein A specific nicks, thus would increase the background signal, making interpretation of data difficult. A tripartite enzyme would be useful for this application since the polymerase would be a fused product with nicking enzyme such as Nt.CviPII. Here we hypothesize a tripartite fusion protein consisting of Protein A-DNA Pol I-Nt.CviPII (fusion enzyme) would remain bound to antibody and only can nick the vicinity of binding, thus allow the polymerase module to perform NEAT-Seq labeling reaction as demonstrated in Examples 2 and 3, and FIG. 6A-6B. The tripartite fusion enzyme bound to only nicked DNA will be removed by heparin.

Example 8: Methods for Lamin Associated Domain Visualization and Sequencing

The following method was performed as outlined in FIG. 10A-10F.

Preparation of cells including formaldehyde fixation from cell cultures was performed by first crosslinking with 2% formaldehyde (Electron Microscopy Sciences #15710) in PBS for 10 minutes at room temperature. The formaldehyde was removed and the cells washed with 1×PBS. The cells were incubated overnight at 55° C. O/N in 1×PBS.

Cell Permeabilization and Blocking was achieved after removing buffer by covering the cell slides with a second buffer (1×PBS/5% BSA/0.3% Triton X-100) for one hour at room temperature.

Primary/Secondary Antibody Incubation occurred by removing the buffer in the previous step and incubating the cells with primary IgG antibody (concentration dependent on manufacture's recommendation generally 1 µg/ml) in PBS/0.3% Triton X-100/0.1% BSA overnight at 4° C., or at room temperature for 2 hours.

The cells were washed with PBS/0.3% Triton X-100 for 10 minutes.

The cells were then treated with Goat anti-Mouse IgG (H+L) Superclonal or Goat anti-Rabbit IgG (H+L) Superclonal, Secondary Antibody (depending on species of primary antibody), Alexa Fluor 488 conjugate (Thermo Fisher Scientific, Waltham, Mass.) at a dilution of 1:2000 in PBS/0.3% Triton X-100/0.1% BSA for 45 minutes at room temperature.

The cells were then washed with 1 ml each well in PBS/0.3% Triton X-100 3×, for 10 minutes.

Low NaCl Wash and Heparin Preloading: In order to prevent Nt.CviPII-Protein G+L or Nt.CviPII-Protein A from preferentially binding non-specifically to nuclear DNA, the active site of Nt.CviPII was competitively bound with heparin. Heparin becomes complexed with the Nt.CviPII at low $NaCl_2$ concentrations. This does not interfere with the binding of Protein A or G to the antibody associated with a target on or in the DNA. After incubation, a 1M $NaCl_2$ wash removed the heparin from the active site of Nt.CviPII, rendering the enzyme competent to initiate a DNA nick near the site of the antibody.

Low NaCl Heparin Wash: Add 1 ml each well heparin wash buffer (20 mM KPO4 pH 7.0, 1 mM EDTA, 20 mM NaCl2, 0.3% Triton X-100, 0.1% BSA and 1/mg/ml Heparin Sodium Salt (Sigma-Aldrich #H3149) for 15 minutes. The Nt.CviPII-Protein G (~2000 U/ml) was diluted by adding 5 µl (10 units) of enzyme into 5 mls of the above buffer which was then incubated for 10 minutes on ice. The cells were then washed with 20 mM KPO4 pH 7.0, 1 mM EDTA, 1M NaCl2, and 0.3% Triton X-100 and then 1×PBS to remove any residual NaCl from the cells.

Nicking Enzyme Extension Reaction: The following components were combined: 0.5 ml NEBuffer 2 containing magnesium salts (New England Biolabs #67002S), 10 µl DNA polymerase I (New England Biolabs #M0209S), 15 µl of dATP, dTTP and dGTP (30 µM) (New England Biolabs #N04465), 5 µl (6 µM) Texas Red-5-dATP (PerkinElmer, Waltham, Mass. #NEL47100EA), 5 µl Biotin-14 dCTP (0.4 mM concentration, Thermo Fisher Scientific, Waltham, Mass. #19518018). 2 µl Biotin-14 dATP (0.4 mM concentration, Thermo Fisher Scientific, Waltham, Mass. #19524016) and 2.5 µl 5meCTP, (10 mM concentration, New England Biolabs, Ipswich, Mass. #N03565). This was incubated for 1 hour and then washed with 20 mM KPO4 pH 7.0, 1 mM EDTA, 1M NaCl2, and 0.3% Triton X-100 followed by 1×PBS. The cells were mounted on cover slips and the nuclei stained with SlowFade Gold Antifade Mountant with DAPI (Thermo Fisher Scientific, Waltham, Mass. #S36938) and visualized on a Zeiss confocal microscope. The results are shown in FIG. 14A-14C and FIG. 15A-15F.

NextGen Sequencing Library Construction for labeled non-mounted cells: The Monarch® Genomic DNA Purification Kit (New England Biolabs, Ipswich, Mass. #T3010S) was used for tissue culture cells. 500 ng of purified genomic DNA is incubated with 50 µl of 10×NEBuffer2, and 1 µl (2 units) of Nt.CviPII nicking enzyme (New England Biolabs, Ipswich, Mass. #R0626S, 2000 units/ml) and incubated at 37° C. overnight. 30 µl of Streptavidin Magnetic Beads (New England Biolabs, Ipswich, Mass. #514205) were added to the reaction, resuspended in 1 ml of B&W buffer (10 mM Tris-HCl pH 8.0, 1 mM EDTA, 1.3 M NaCl) and incubated at 4° C. for 2 hours. The streptavidin bead were bound to the library twice on the magnet using B&W buffer supplemented with 0.05% Triton X-100 and once with 1×TE plus 0.05% Triton X-100. After a final wash in 0.1×TE, the protocol was followed to generate libraries with fragmented DNA (up to 1 µg) using the NEBNext® Ultra II DNA Library Prep Kit (New England Biolabs, Ipswich, Mass. #E7645S). All steps including the barcode adapter PCR were accomplished on the beads. There was no size selection step. The results are shown in FIGS. 13 and 15A-15F.

Example 9: Reduced Background Under Optionally High Concentrations of NEFP to Detect Rare Target Events in Nuclear Chromatin Media from cell cultures or tissues was replaced by a heparin salt solution before addition of NEFP plus heparin.

1 ml heparin wash buffer (20 mM Kpo4 pH 7.0, 1 mM EDTA, 20 mM NaCl2, 0.3% Triton X-100, 0.1% BSA and 1/mg/ml Heparin Sodium Salt (SigmaAldrich #H3149) was added to each cell well or tissue slide and incubated for 15 minutes. The Triton X caused cytoplasm and nucleus to become porous for receiving the antibody for binding target and for receiving the NEFP for binding to the antibody.

A stock solution of Nt.CviPII-Protein G/L (~2000 U/ml) was diluted by adding 2.5 μl (5 units) of the NEFP into 5 mls of preload heparin buffer (20 mM Kpo4 pH 7.0, 1 mM EDTA, 20 mM NaCl2, 0.3% Triton X-100, 0.1% BSA and 1/mg/ml Heparin Sodium Salt (Sigma-Aldrich, St. Louis, Mo. #H3149) and incubated for 10 minutes on ice. 800 μl of the NEFP in the preload buffer was added to each well containing cells and incubated for 45 minutes at room temperature. This permitted the NEFP to find and bind to the antibody-target in nuclear chromatin.

The residual unbound NEFP was then removed by washing the cells for 15 minutes at room temperature with 20 mM Kpo4 pH 7.0, 1 mM EDTA, 1M NaCl2, and 0.3% Triton X-100. The cells were then washed with 1×PBS for 10 minutes at room temperature to remove any residual high $NaCl_2$ from the cells.

NEBuffer 2 containing magnesium ions was then added to the cells to permit the nicking endonuclease in the NEFP to nick DNA.

What is claimed is:

1. A method for identifying a DNA location of a target protein that is on chromosomal DNA in a sample, comprising:
   (a) combining a nicking endonuclease fusion protein (NEFP) and a sample under conditions wherein the NEFP is reversibly prevented from binding to the chromosomal DNA; wherein
   (i) the NEFP comprises a nicking endonuclease and a protein A or protein G domain; and
   (ii) a target protein bound to chromosomal DNA is present in the sample, wherein the target protein is directly or indirectly bound to a target protein-specific antibody, under conditions by which the protein A or protein G domain in the NEFP binds to the constant region of the target protein-specific antibody;
   (b) allowing nicking endonuclease that is bound to the target protein-specific antibody in (a) to nick the chromosomal DNA in a buffer containing magnesium or manganese ions for permitting the nicking activity of the NEFP;
   (c) nick translating the nicked chromosomal DNA with a strand displacing polymerase in the presence of a mixture of dNTPs wherein one or more dNTPs in the mixture is modified for blocking secondary nicking;
   (d) sequencing of the nick translated DNA produced in step (c) to identify the DNA location of the target protein on the chromosomal DNA.

2. The method according to claim 1, wherein the target protein is a DNA binding protein.

3. The method according to claim 1, wherein step (a) is done in a first buffer, wherein the first buffer contains a heparin and an inorganic salt.

4. The method according to claim 1, wherein the sample is a cell sample.

5. The method according to claim 1, wherein step (a) or a step prior to step (a) is done at a temperature in the range of 20° C.-100° C.

6. The method according to claim 1, wherein the method is performed at a single temperature.

7. The method according to claim 3, wherein step (a) further comprises washing away unbound NEFP and the heparin by replacing the first buffer with a second buffer containing an inorganic salt that is at a concentration that is higher than the concentration of the inorganic salt in the first buffer.

8. The method according to claim 1, wherein the NEFP comprises a nicking endonuclease fused to a Protein A or Protein G domain or any combination thereof in tandem.

9. The method according to claim 1, wherein the nicking endonuclease in the NEFP is Nt.CviPII or gHNH.

10. The method according to claim 1, wherein the one or more modified nucleotides are selected from the group consisting of d5mCTP, biotinylated CTP and a dye labeled dNTP.

11. The method according to claim 1, wherein the method comprises immobilizing the nick translated DNA produced in step (c), before step (d).

12. The method according to claim 11, further comprising preparing a library from the immobilized DNA.

13. The method according to claim 12, comprising sequencing the library and identifying the location of the target protein in the DNA sequence.

14. The method according to claim 1, wherein the target protein is diagnostic for cancer or treatment of cancer, the method further comprises determining the presence of the diagnostic target by microscopy and sequencing on the same cell sample or biopsy from a patient.

* * * * *